(12) United States Patent
Buschmann et al.

(10) Patent No.: US 9,393,220 B2
(45) Date of Patent: Jul. 19, 2016

(54) CO-CRYSTALS OF TRAMADOL AND NSAIDS

(71) Applicant: LABORATORIOS DEL DR. ESTEVE, S.A., Barcelona (ES)

(72) Inventors: Helmut Heinrich Buschmann, Walheim (DE); Lluis Sola Carandell, Tarragona (ES); Jordi Benet Buchholz, Tarragona (ES); Jordi Carles Ceron Bertran, Tarragona (ES); Carlos Ramon Plata Salaman, Barcelona (ES); Nicolas Tesson, L'Hospitalet de Llobregat (ES)

(73) Assignee: LABORATORIES DEL DR. ESTEVE, S.A., Barcelona (ES)

( * ) Notice: Subject to any disclaimer, the term of this patent is extended or adjusted under 35 U.S.C. 154(b) by 0 days.

(21) Appl. No.: 14/324,448

(22) Filed: Jul. 7, 2014

(65) Prior Publication Data

US 2014/0350110 A1    Nov. 27, 2014

Related U.S. Application Data

(62) Division of application No. 13/124,027, filed as application No. PCT/EP2009/007451 on Oct. 16, 2009, now abandoned.

(30) Foreign Application Priority Data

Oct. 17, 2008   (EP) .................................. 08384012

(51) Int. Cl.
| | |
|---|---|
| *C07C 59/64* | (2006.01) |
| *C07C 217/74* | (2006.01) |
| *A61K 31/135* | (2006.01) |
| *A61K 31/192* | (2006.01) |
| *A61K 31/137* | (2006.01) |
| *A61K 31/635* | (2006.01) |

(52) U.S. Cl.
CPC ............. *A61K 31/135* (2013.01); *A61K 31/137* (2013.01); *A61K 31/192* (2013.01); *A61K 31/635* (2013.01); *C07C 59/64* (2013.01); *C07C 217/74* (2013.01); *C07C 2101/14* (2013.01)

(58) Field of Classification Search
None
See application file for complete search history.

(56) References Cited

U.S. PATENT DOCUMENTS

| | | |
|---|---|---|
| 2003/0147948 A1 | 8/2003 | Shinoda et al. |
| 2004/0076669 A1 | 4/2004 | Bartholomaus et al. |
| 2006/0172006 A1 | 8/2006 | Lenaerts et al. |
| 2007/0026078 A1 | 2/2007 | Almarsson et al. |
| 2007/0141144 A1 | 6/2007 | Roberts et al. |
| 2008/0031950 A1 | 2/2008 | Sesha |

FOREIGN PATENT DOCUMENTS

| | | |
|---|---|---|
| EP | 0546676 A | 6/1993 |
| EP | 2022778 A | 2/2009 |
| WO | 00/51685 | 8/2000 |
| WO | 2004/078162 A2 | 9/2004 |
| WO | 2008/064854 A | 6/2008 |
| WO | 2009/018959 A1 | 2/2009 |
| WO | 2009143295 A1 | 11/2009 |
| WO | 2011044962 A1 | 4/2011 |

OTHER PUBLICATIONS

Burke et al. (British Journal of Anaesthesia, 2002, 88(4), 563).*
STN Registry of 22204-53-1, (Naproxen), 1984.*
STN Registry of 26159-34-2, (Naproxen), 1984.*
*Merck & Co. Inc. v. Biocraft Laboratories Inc.*, 10 USPQ2d 1843 (Fed. Cir. 1989) (U.S. Court of Appeals Federal Circuit, 1989).
International Search Report for PCT/EP2009/007451 dated Dec. 2, 2009.
Shan et al., The Role of Cocrystals in Pharmaceutical Science, Drug Discovery Today, Elsevier, Rahway NJ, US, vol. 13, No. 9-10, May 1, 2008, pp. 440-446.
Trask, An Overview of Pharmaceutical Cocrystals as Intellectual Property. Molecular Pharmaceutics, American Chemical Society, US, vol. 4, No. 3, Jan. 1, 2007, pp. 301-309.
Remenar et al., Celecoxib: Nicotinamide Dissociation: Using Excipients to Capture the Cocrystal's Potential, Molecular Pharmaceutics, vol. 4, No. 3, May 2007, pp. 386-400.

* cited by examiner

*Primary Examiner* — Sudhakar Karakam
*Assistant Examiner* — Jennifer C Sawyer
(74) *Attorney, Agent, or Firm* — Heslin, Rothenberg, Farley & Mesiti, P.C.

(57) ABSTRACT

The present invention relates to co-crystals of tramadol and co-crystal formers selected from NSAIDs, processes for preparation of the same and their uses as medicaments or in pharmaceutical formulations, more particularly for the treatment of pain.

14 Claims, 11 Drawing Sheets

CO-CRYSTALS OF TRAMADOL AND NSAIDS

CROSS REFERENCE TO RELATED APPLICATIONS

This application is a divisional application of U.S. patent application Ser. No. 13/124,027, filed Apr. 13, 2011, which was a U.S. National Phase filing under 35 U.S.C. §371 of International Application PCT/EP2009/007451, filed Oct. 16, 2009, and published as WO 2010/043412 on Apr. 22, 2010. PCT/EP2009/007451 claimed benefit of priority from European Patent Application No. EP 08384012.4, filed Oct. 17, 2008. The entire contents of each of the prior applications are incorporated herein by reference.

The present invention relates to co-crystals of tramadol and NSAIDs (Non steroidal anti-inflammatory drugs), processes for preparation of the same and their uses as medicaments or in pharmaceutical formulations, more particularly for the treatment of pain.

Pain is a complex response that has been functionally categorized into sensory, autonomic, motor, and affective components. The sensory aspect includes information about stimulus location and intensity while the adaptive component may be considered to be the activation of endogenous pain modulation and motor planning for escape responses. The affective component appears to include evaluation of pain unpleasantness and stimulus threat as well as negative emotions triggered by memory and context of the painful stimulus.

In general, pain conditions can be divided into chronic and acute. Chronic pain includes neuropathic pain and chronic inflammatory pain, for example arthritis, or pain of unknown origin, as fibromyalgia. Acute pain usually follows non-neural tissue injury, for example tissue damage from surgery or inflammation, or migraine.

There are many drugs that are known to be useful in the treatment or management of pain.

Opioids are frequently used as analgesics in pain. Derivatives of morphine are indicated for the treatment of moderate to acute pain in human. The analgesic effect is obtained through their action on morphinic receptors, preferably the μ-receptors. Among these derivatives of morphine, may be mentioned morphine, codeine, pethidine, dextropropoxyphenemethadone, lenefopan and others.

One of the morphinic derivatives that has shown very good results when orally administrated, and which is extensively marketed, is Tramadol, also available as a physiologically acceptable salt, particularly as a chlorohydrate. Tramadol, whose chemical name is 2-(dimethylaminomethyl)-1-(3-methoxyphenyl)cyclohexanol, has the following formula:

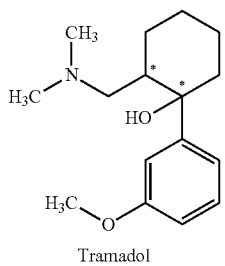 [SMILES: COc1cccc(C2(O)CCCCC2CN(C)C)c1]

Tramadol

This structure shows two different chiral centers and thus may exist in different diastereoisomers among which the tramadol is the cis-diastereisomer: (1R,2R), or (1S,2S), both also known as (+)-tramadol and (−)-tramadol and both of which contribute in different ways to its activity.

From the art it appears that this compound is neither fully opioid-like, nor non-opioid-like. Some studies have demonstrate that tramadol is an opioid agonist, whereas clinical experience indicates that it lacks many of the typical side effects of opioids agonist, for example respiratory depression, constipation or tolerance.

Due to their drawbacks, opioids cannot always be given repeatedly or at higher doses as analgesics to treat pain. The side effects of opioids are known in the art including e.g. J. Jaffe in "Goodman and Gilman's, The Pharmacological Basis of Therapeutics", 8$^{th}$ edition; Gilman et al.; Pergamon Press, New York, 1990, Chapter 22, pages 522-573.

Consequently it has been proposed to combine opioids with other drugs that are not opioid analgesic agents, in order to lower the amount of opioids needed to produce an equivalent degree of analgesia. Among these combinations, the association of tramadol with nonsteroidal anti-inflammatory drugs (NSAIDs) has been reported to be of particular interest (EP-0 546 676).

Thus it was the objective of the current invention to provide new means of improving the properties of tramadol, especially in regard to the treatment of pain, by providing new drugable forms of tramadol.

Especially desirable improvements/advantages of the new drugable form would include:
improvement of physicochemical properties in order to facilitate the formulation, the manufacture, or to enhance the absorption and/or the bioavailability: thus being more active when compared to tramadol base or hydrochloride salt; or
providing a form tramadol with a further active agent having a beneficial pharmacological effect in itself, thus allowing for a highly efficient dose/weight relation of the final active principle or even
allowing the use of a lower therapeutic dose of either tramadol and the further active agent, an NSAID, or of both;
having a synergistic effect through the combination of tramadol and the further active agent, an NSAID, in the same new drugable form; or further
having the bitter taste of tramadol removed or ameliorated;
being easily obtainable, easy to manufacture or
allowing more flexibility in formulating, or facilitating its formulation,
being highly soluble, thus allowing better dissolution rates, especially if dissolving in an aqueous physiological surrounding, or
improving stability of the co-crystal in comparison to the physical mixture of Tramadol/Active Agent (an NSAID) at the same ratio;
allowing new routes of administration; also
allowing—if necessary—to combine tramadol with a chemically usually non-compatible active agent in the same formulation or even in immediate contact, without having to isolate tramadol; or finally
minimizing/reducing the side effects, especially the severe side effects, assigned to tramadol.

Other desirable improvements/advantages of the new drugable form would include being active in diseases or symptoms in which current treatment is insufficient like sciatica or frozen shoulder.

Most desirably the new drugable forms should combine more than one, most of these advantages.

This objective was achieved by providing new co-crystals of tramadol. It was found that Tramadol was able to form Co-crystals with NSAIDs. These co-crystals show improved properties if compared to tramadol alone, and also good analgesic activity. The co-crystals thus obtained have a specific stoichiometry which depends upon the structure of each NSAID. Under the proper circumstance this is also another advantage of these new solid drugable forms possibly achieving some modulation of the pharmacological effects. While APIs (Active Pharmaceutical Ingredients) like tramadol in general have been recognized to form crystalline polymorphs, solvates, hydrates and amorphous forms for a number of years, there is little knowledge about which APIs will form co-crystals. Co-crystals are a specific type of crystalline form which provide a new avenue to modulate the API form and thus to modulate API properties. Co-crystals contain an API and at least one other component which crystallize together. Selection of the other component helps determine whether a co-crystal will form and what properties the co-crystal will have. Just as a polymorph, solvate, hydrate or amorphous form of an API can modulate stability, solubility, and hygroscopicity, a co-crystal can modulate those same properties.

Thus the main object of the present invention is a co-crystal comprising tramadol either as a free base or as a physiologically acceptable salt and at least one NSAID.

"Drugable form (of tramadol)" as used herein is defined as any form (salt, amorphous crystal, solution, dispersion, mixture etc,) that tramadol might take which still can be formulated into a pharmaceutical formulation usable as a medicament to treat a disease or a symptom, especially pain.

"Co-Crystal" as used herein is defined as a crystalline material comprising two or more compounds at ambient temperature (20 to 25° C., preferably 20° C.), of which at least two are held together by weak interaction, wherein at least one of the compounds is a co-crystal former. Weak interaction is being defined as an interaction which is neither ionic nor covalent and includes for example: hydrogen bonds, van der Waals forces, and π-π interactions. Solvates of tramadol that do not further comprise a co-crystal former are not co-crystals according to the present invention. The co-crystals may however, include one or more solvate molecules in the crystalline lattice. Just for the sake of clarity the distinction between crystalline salt and a co-crystal has to be stressed here. An API bound to another compound forming a salt by means of ionic interaction can be considered as one "compound" according to the invention, but it cannot be considered as two compounds by itself.

In scientific literature there currently is some discussion on the proper use of the word co-crystal (see for example Desiraju, *Cryst. Eng. Comm.*, 2003, 5(82), 466-467 and Dunitz, *Cryst. Eng. Comm.*, 2003, 5(91), 506). A recent article by Zawarotko (Zwarotko, *Crystal Growth & Design*, Vol. 7, No. 1, 2007, 4-9) gives a definition of co-crystal which is in line with the definition given above and thus also is a definition of "co-crystal" according to this invention. According to this article "a co-crystal is a multiple component crystal in which all components are solid under ambient conditions when in their pure form. These components consist of a target molecule or ion and a molecular co-crystal former(s); when in a co-crystal, they coexist at a molecular level within a single crystal".

"Co-crystal former" as use herein is defined as a molecule being an active agent selected from NSAIDs, and with which tramadol is able to form co-crystals.

"Active agents" are APIs which show a pharmaceutical effect and thus can be identified as being pharmaceutically active. In a more narrow sense this definition is encompassing all APIs being marketed or under clinical trial for the treatment of diseases. "Active agents with analgesic activity" are APIs (Active Pharmaceutical Ingredients) which show efficacy in well-known animal models of pain and thus can be identified as being analgesics. In a more narrow sense this definition is encompassing all APIs being marketed or under clinical trial for a labelling including an indication falling under the definition of pain, including also migraine. These indications might include acute pain, chronic pain, neuropathic pain, hyperalgesia, allodynia or cancer pain, including diabetic neuropathy or diabetic peripheral neuropathy, osteoarthritis or fibromyalgia and all their subforms. Examples of "active agents with analgesic activity" include NSAIDs like naproxen or ibuprofen, pregabalin or tramadol and its N-desmethyl-metabolite.

"Pain" is defined by the International Association for the Study of Pain (IASP) as "an unpleasant sensory and emotional experience associated with actual or potential tissue damage, or described in terms of such damage (IASP, Classification of chronic pain, $2^{nd}$ Edition, IASP Press (2002), 210). Even though pain is always subjective its causes or syndromes can be classified.

According to the IASP "allodynia" is defined as "a pain due to a stimulus which does not normally provoke pain" (IASP, Classification of chronic pain, $2^{nd}$ Edition, IASP Press (2002), 210). Even though the symptoms of allodynia are most likely associated as symptoms of neuropathic pain this is not necessarily the case so that there are symptoms of allodynia not connected to neuropathic pain though rendering allodynia in some areas broader than neuropathic pain.

The IASP further draws the following difference between "allodynia", "hyperalgesia" and "hyperpathia" (IASP, Classification of chronic pain, $2^{nd}$ Edition, IASP Press (2002), 212):

| Allodynia | Lowered threshold | Stimulus and response mode differ |
|---|---|---|
| Hyperalgesia | Increased response | Stimulus and response rate are the same |
| Hyperpathia | Raised threshold; Increased response | Stimulus and response rate may be the same or different |

According to the IASP "neuropathy" is defined as "a primary lesion or dysfunction in the nervous system" (IASP, Classification of chronic pain, $2^{nd}$ Edition, IASP Press (2002), 211). Neuropathic pain may have central or peripheral origin.

"Sciatica" or "sciatic neuritis is defined herein as a set of symptoms including pain that derive from irritation of the sciatic nerve or its roots, "Frozen shoulder" or "adhesive capsulitis" is defined herein as a symptom wherein the connective tissue surrounding the shoulder joint or the shoulder capsule itself, is causing chronic pain, becoming inflamed and stiff.

"Ankylosing spondylitis" or "Morbus Bechterew" is a chronic, inflammatory arthritis and autoimmune disease. It mainly affects joints in the spine and the sacroilium in the pelvis, causing eventual fusion of the spine.

In one preferred embodiment of the co-crystal according to the invention, the NSAID has at least one functional group from the group consisting of ether, thioether, alcohol, thiol, aldehyde, ketone, thioketone, nitrate ester, phosphate ester, thiophosphate ester, ester, thioester, sulfate ester, carboxylic acid, phosphonic acid, phosphinic acid, sulfonic acid, amide, primary amine, secondary amine, ammonia, tertiary amine, thiocyanate, cyanamide, oxime, nitrile, diazo, organohalide, nitro, s-heterocyclic ring, thiophene, n-heterocyclic ring, pyrrole, o-heterocyclic ring, furan, epoxide, peroxide, hydroxamic acid, imidazole, and pyridine;

preferably wherein the NSAID has at least one functional group from the group consisting of alcohol, thiol, ester, carboxylic acid, primary amine, secondary amine, tertiary amine.

In another embodiment the NSAID has at least one functional group from the group consisting of alcohol, ester, or carboxylic acid.

In a further embodiment of the co-crystal according to the invention, the NSAID/s is/are chosen in such a way that if compared to either tramadol alone, or to a mixture of tramadol and the corresponding active agent/s:

the solubility of the co-crystal is increased; and/or
the dose response of the co-crystal is increased; and/or
the efficacy of the co-crystal is increased; and/or
the dissolution of the co-crystal is increased; and/or
the bioavailability of the co-crystal is increased; and/or
the stability of the co-crystal is increased; and/or
the hygroscopicity of the co-crystal is decreased; and/or
the form diversity of the co-crystal is decreased; and/or
the morphology of the co-crystal is modulated.

"Mixture of tramadol and the corresponding active agent/s" is defined as a mixture of the active agent or agents in question (the NSAID/s) with tramadol which is only a physical mixture without any coupling forces between the compounds and thus neither includes salts nor another co-crystal.

In a further embodiment of the co-crystal according to the invention, the molar ratio between tramadol and the NSAID is different from 1. This might have the advantage of allowing the development of a non-equimolar ratio between tramadol and the active agent/s in a fixed dose with all the advantages of the co-crystal.

NSAIDs have analgesic activity in a number of pain symptoms, with acetyl salicylic acid known under its trademark aspirin—despite being more than 100 years old—being an outstandingly used pharmaceutical. Besides Aspirin other NSAIDs (and COX-INHIBITORS) whose use generally is also centered on anti-inflammatory action like Ibuprofen, naproxen or diclofenac are among the worldwide most frequently applied pharmaceutical compounds. The basis of their activity is inhibition of cyclooxygenase (COX), one of the two activities of prostaglandine endoperoxide synthase (PGHS). It is a key enzyme in the prostaglandin pathway. Preferred NSAIDs, are those with a carboxylic acid function. Preferred examples include salicylates, anthranilates, arylacetic acids/arylalkanoic acids, and arylpropionic acids.

It is debated in literature whether paracetamol/acetaminophen is to be considered an NSAID. Thus—in an embodiment of this invention—paracetamol/acetaminophen is not considered an NSAID and is therefore excluded/disclaimed from the (list of) NSAIDs (Co-crystal formers) according to this invention.

In a further embodiment of the co-crystal according to the invention, the NSAID is selected from:

Acetylsalicylic Acid;
Triflusal;
HTB (2-hydroxy-4-trifluoromethyl benzoic acid);
Diflunisal;
Meclofenamic acid;
Mefenamic acid;
Niflumic acid;
Flufenamic acid;
Diclofenac;
Lonazolac;
Acemetacin;
Indomethacin;
Tolmetin;
Sulindac;
Etodolac;
Keterolac;
Flurbiprofen;
(RS)-Flurbiprofen;
Esflurbiprofen;
Ibuprofen;
(RS)-Ibuprofen;
S-(+)-Ibuprofen;
Ketoprofen;
(rac)-Ketoprofen;
R-(−)-Ketoprofen;
Bermoprofen;
Pelubiprofen;
Tenosal;
Aceneuramic acid;
Pirazolac;
Xinoprofen;
Flobufen;
Anirolac;
Zoliprofen;
Bromfenac;
Pemedolac;
Dexpemedolac;
Bindarit;
Romazarit;
Naproxen;
(S)-Naproxen;
(R)-Naproxen;
Tiaprofenic acid;
Ketorolac;
Fenbufen;
Fenoprofen;
Flobufen; or
Oxaprozin.

In general all of these NSAIDs which have at least one stereogenic center are to be understood as being included herein in their racemic form or as diastereoisomers or enantiomers or mixtures thereof.

In a further embodiment the NSAID is a Coxib, a selective COX-2 inhibitor. Therefore, another preferred embodiment of the invention is a pharmaceutical compound comprising Tramadol and at least one COX-inhibitor selected from an NSAID being a Coxib. Examples of Coxibs are: celecoxib, etoricoxib, lumiracoxib, parecoxib, rofecoxib, valdecoxib, and cimicoxib.

Thus, especially preferred is a pharmaceutical compound comprising tramadol and celecoxib, preferably a pharmaceutical compound comprising (rac)-tramadol.HCl and celecoxib.

In a further embodiment of the co-crystal according to the invention, the NSAID is selected from:

Acetylsalicylic Acid;
Triflusal;
HTB (2-hydroxy-4-trifluoromethyl benzoic acid);
Diflunisal;
Meclofenamic acid;
Mefenamic acid;
Niflumic acid;
Flufenamic acid;
Diclofenac;
Lonazolac;
Acemetacin;
Indomethacin;
Tolmetin;
Sulindac;

Etodolac;
Keterolac;
Flurbiprofen;
(RS)-Flurbiprofen;
Esflurbiprofen;
Ibuprofen;
(RS)-Ibuprofen;
S-(+)-Ibuprofen;
Ketoprofen;
(rac)-Ketoprofen;
R-(−)-Ketoprofen;
Bermoprofen;
Pelubiprofen;
Tenosal;
Aceneuramic acid;
Pirazolac;
Xinoprofen;
Flobufen;
Anirolac;
Zoliprofen;
Bromfenac;
Pemedolac;
Dexpemedolac;
Bindarit;
Romazarit;
Naproxen;
(S)-Naproxen;
(R)-Naproxen;
Tiaprofenic acid;
Ketorolac;
Fenbufen;
Fenoprofen;
Flobufen; or
Oxaprozin; or
Celecoxib,
Etoricoxib,
Lumiracoxib,
Parecoxib,
Rofecoxib,
Valdecoxib, or
Cimicoxib.

The term "salt" is to be understood as meaning any form of tramadol or the NSAID according to the invention in which this assumes an ionic form or is charged and is coupled with a counter-ion (a cation or anion) or is in solution. By this are also to be understood complexes of tramadol or the NSAID with other molecules and ions, in particular complexes which are complexed via ionic interactions. This also includes physiologically acceptable salt.

The term "solvate" according to this invention is to be understood as meaning any form of the tramadol or NSAID in which the compound has attached to it via non-covalent binding another molecule (most likely a polar solvent) especially including hydrates and alcohol solvates, e.g. methanol solvate.

A highly interesting NSAID to be the co-crystal former with tramadol is the marketed drug naproxen. The chemical name of its (S)-enantiomer, the marketed (S)-naproxen, is (S)-(6-methoxy-2-naphtyl)propionic acid, and which is also described as a physiologically acceptable salt. It has an empirical formula of $C_{14}H_{14}O_3$, an Mp of 153° C. and a pKa of 4.2.

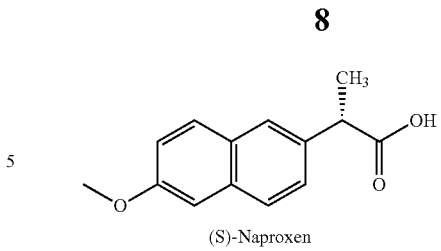

(S)-Naproxen

The (R)-enantiomer, the (R)-naproxen, whose chemical name is (R)-(6-methoxy-2-naphtyl)propionic acid, having the same formula of $C_{14}H_{14}O_3$, Mp of 153° C. and pKa of 4.2, shows the following formula.

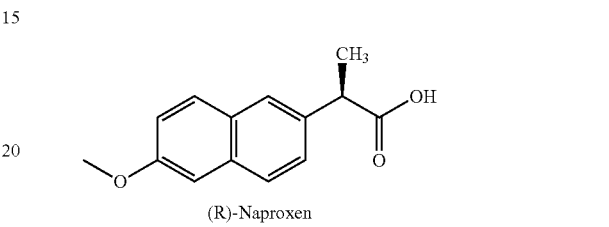

(R)-Naproxen

Thus, another very preferred aspect of the invention relates to a co-crystal according to the invention, wherein the NSAID is naproxen, its enantiomers or salts thereof. Especially it refers to a co-crystal according to the invention, wherein the NSAID is (S)-naproxen or (R)-naproxen.

Another embodiment of the invention relates to a co-crystal according to the invention, wherein the tramadol is (−)-tramadol or (+)-tramadol.

As illustrated in more detail below tramadol and especially its enantiomers (+)-tramadol and (−)-tramadol form co-crystals with naproxen, especially with (S)-naproxen and (R)-naproxen. Generally co-crystals obtained have a specific stoichiometry which depends upon the structure of each co-crystal forming NSAID. In this specific case of the co-crystal between tramadol and naproxen being the co-crystal former the molecular ratio between tramadol and naproxen is 1 to 2.

In a further preferred embodiment of the invention, co-crystal according to the invention, is selected from
- a co-crystal comprising (−)-tramadol either as a free base or as a physiologically acceptable salt and (S)-naproxen;
- a co-crystal comprising (+)-tramadol either as a free base or as a physiologically acceptable salt and (R)-naproxen;
- a mixture of enantiomers of co-crystals comprising (−)-tramadol either as a free base or as a physiologically acceptable salt and (S)-naproxen and co-crystals comprising (+)-tramadol either as a free base or as a physiologically acceptable salt and (R)-naproxen;
- any of the co-crystals above being solvate co-crystals, preferably being alcohol solvate co-crystals, most preferably being methanol solvate co-crystals.

In a highly preferred embodiment of these selected co-crystals, the molecular ratio between the tramadol and naproxen is 1:2.

In a preferred embodiment of a co-crystal with a molecular ratio between the tramadol and naproxen of 1:2 according to the invention comprising (−)-tramadol either as a free base or as a physiologically acceptable salt and (S)-naproxen or comprising (+)-tramadol either as a free base or as a physiologically acceptable salt and (R)-naproxen, or mixture of enantiomers of these co-crystals, the co-crystal shows a Powder X-Ray Diffraction pattern with peaks [2θ] at 4.3, 8.7, 9.5, 10.2, 10.6, 11.3, 12.1, 12.7, 13.2, 13.7, 14.3, 14.6, 14.8, 15.5, 15.7, 16.0, 16.2, 17.0, 17.4, 17.9, 18.1, 18.7, 19.1, 19.4, 19.7, 20.1, 20.5, 20.8, 21.1, 21.4, 21.6 and 21.8 [°].

The 2θ values were obtained using copper radiation ($Cu_{K\alpha 1}$ 1.54060 Å).

In a preferred embodiment of a co-crystal with a molecular ratio between the tramadol and naproxen of 1:2 according to the invention comprising (−)-tramadol either as a free base or as a physiologically acceptable salt and (S)-naproxen or comprising (+)-tramadol either as a free base or as a physiologically acceptable salt and (R)-naproxen, or mixture of enantiomers of these co-crystals, the co-crystal shows a Fourier Transform Infra Red pattern with absorption bands at 3247, 2942, 1699, 1633, 1605, 1583, 1485, 1380, 1271, 1223, 1160, 1029, 851, 789 and 704 $cm^{-1}$.

In a preferred embodiment of a co-crystal with a molecular ratio between the tramadol and naproxen of 1:2 according to the invention comprising (−)-tramadol either as a free base or as a physiologically acceptable salt and (S)-naproxen or comprising (+)-tramadol either as a free base or as a physiologically acceptable salt and (R)-naproxen, or enantiomeric mixtures of these co-crystals, the co-crystal has a monoclinic unit cell with the following dimensions:
a=9.512(2) Å
b=40.5736(11) Å
c=10.323(4) Å
α=90°
β=96.29(1)°
γ=90°.

In a preferred embodiment of a co-crystal with a molecular ratio between the tramadol and naproxen of 1:2 according to the invention comprising (−)-tramadol either as a free base or as a physiologically acceptable salt and (S)-naproxen or comprising (+)-tramadol either as a free base or as a physiologically acceptable salt and (R)-naproxen, or enantiomeric mixtures of these co-crystals, the endothermic sharp peak of the co-crystal corresponding to the melting point has an onset at 82° C.

In another preferred embodiment of a co-crystal with a molecular ratio between the tramadol and naproxen of 1:2 according to the invention comprising (−)-tramadol either as a free base or as a physiologically acceptable salt and (S)-naproxen or comprising (+)-tramadol either as a free base or as a physiologically acceptable salt and (R)-naproxen, or enantiomeric mixtures of these co-crystals, the endothermic sharp peak of the co-crystal corresponding to the melting point has an onset at 82° C. to 84° C.

In another preferred embodiment a co-crystal with a molecular ratio between the tramadol and naproxen of 1:2 according to the invention comprising (+)-tramadol either as a free base or as a physiologically acceptable salt and (R)-naproxen is in the form of a methanol solvate.

In a preferred embodiment of a co-crystal with a molecular ratio between the tramadol and naproxen of 1:2 according to the invention in the form of a methanol solvate comprising (+)-tramadol either as a free base or as a physiologically acceptable salt and (R)-naproxen, the co-crystal shows a Powder X-Ray Diffraction pattern with peaks [2θ] at 4.1, 6.6, 9.0, 9.2, 10.4, 11.0, 11.5, 12.3, 12.5, 12.7, 13.0, 13.2, 13.8, 14.9, 15.4, 16.2, 17.2, 17.6, 18.1, 18.5, 19.1, 19.3, 19.6, 19.9, 20.1, 20.4, 20.9, 21.0, 21.5, 22.0, 22.3 and 22.6 [°].

The 2θ values were obtained using copper radiation ($Cu_{K\alpha 1}$ 1.54060 Å).

In another preferred embodiment of a co-crystal with a molecular ratio between the tramadol and naproxen of 1:2 according to the invention in the form of a methanol solvate comprising (+)-tramadol either as a free base or as a physiologically acceptable salt and (R)-naproxen, the co-crystal shows a Fourier Transform Infra Red pattern with absorption bands at 3523, 3151, 2928, 2861, 2465, 1706, 1632, 1603, 1567, 1485, 1461, 1445, 1417, 1388 and 1362 $cm^{-1}$.

As illustrated in more detail below tramadol forms co-crystals with (S)-naproxen. Generally co-crystals obtained have a specific stoichiometry which depends upon the structure of each co-crystal former. In this specific case of the co-crystal with (S)-naproxen being the NSAID the molecular ratio between Tramadol and (S)-naproxen is 1 to 2.

Highly interesting NSAID to be the co-crystal formers with tramadol are the Coxibs. The most important of these is the marketed drug celecoxib. Its chemical name is 4-[5-(4-methylphenyl)-3-(trifluoromethyl)-pyrazol-1-yl]benzene-sulfonamide. It has an empirical formula of $C_{17}H_{14}F_3N_3O_2S$.

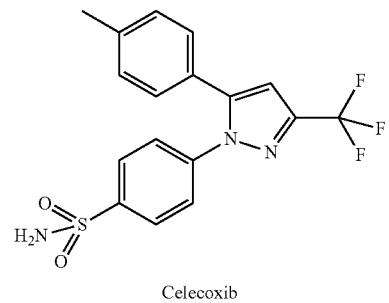 [SMILES: Cc1ccc(-c2cc(C(F)(F)F)nn2-c2ccc(S(N)(=O)=O)cc2)cc1]

Celecoxib

In a further embodiment of the co-crystal according to the invention, the NSAID is selected from:
Celecoxib,
Etoricoxib,
Lumiracoxib,
Parecoxib,
Rofecoxib,
Valdecoxib, or
Cimicoxib.

Another very preferred aspect of the invention relates to a co-crystal according to the invention, wherein the NSAID is celecoxib or salts thereof.

As illustrated in more detail below tramadol—and especially the racemate—forms co-crystals with celecoxib. Generally co-crystals obtained have a specific stoichiometry which depends upon the structure of each co-crystal forming NSAID. In this specific case of the co-crystal between (rac)-tramadol and celecoxib being the co-crystal former the molecular ratio between tramadol and celecoxib is 1 to 1.

In a further preferred embodiment of the invention, co-crystal according to the invention, is selected from
a co-crystal comprising (rac)-tramadol either as a free base or as a physiologically acceptable salt and celecoxib;
a co-crystal comprising (+)-tramadol either as a free base or as a physiologically acceptable salt and celecoxib;
a co-crystal comprising (−)-tramadol either as a free base or as a physiologically acceptable salt and celecoxib; or preferably
a co-crystal comprising (rac)-tramadol.HCl (the hydrochloride salt of tramadol) and celecoxib.

In a highly preferred embodiment of these selected co-crystals, the molecular ratio between the (rac)-tramadol.HCl and celecoxib is 1:1.

In a preferred embodiment of a co-crystal with a molecular ratio between (rac)-tramadol.HCl and celecoxib of 1:1 according to the invention, the co-crystal shows a Powder X-Ray Diffraction pattern with peaks [2θ] at 7.1, 9.3, 10.2, 10.7, 13.6, 13.9, 14.1, 15.5, 16.1, 16.2, 16.8, 17.5, 18.0, 19.0, 19.5, 19.9, 20.5, 21.2, 21.3, 21.4, 21.8, 22.1, 22.6, 22.7, 23.6, 24.1, 24.4, 25.2, 26.1, 26.6, 26.8, 27.4, 27.9, 28.1, 29.1, 29.9, 30.1, 31.1, 31.3, 31.7, 32.5, 32.8, 34.4, 35.0, 35.8, 36.2 and 37.2 [°].

The 2θ values were obtained using copper radiation ($Cu_{K\alpha 1}$ 1.54060 Å).

In a preferred embodiment of a co-crystal with a molecular ratio between (rac)-tramadol.HCl and celecoxib of 1:1 according to the invention, the co-crystal shows a Fourier Transform Infra Red pattern with absorption bands at 3481.6 (m), 3133.5 (m), 2923.0 (m), 2667.7 (m), 1596.0 (m), 1472.4 (m), 1458.0 (m), 1335.1 (m), 1288.7 (m), 1271.8 (m), 1168.7 (s), 1237.3 (m), 1168.7 (s), 1122.6 (s), 1100.9 (m), 1042.2 (m), 976.8 (m), 844.6 (m), 820.1 (m), 786.5 (m) 625.9 (m) $cm^{-1}$.

In a preferred embodiment of a co-crystal with a molecular ratio between (rac)-tramadol.HCl and celecoxib of 1:1 according to the invention, the co-crystal has an orthorhombic unit cell with the following dimensions:
a=11.0323(7) Å
b=18.1095(12) Å
c=17.3206(12) Å

In a preferred embodiment of a co-crystal with a molecular ratio between (rac)-tramadol.HCl and celecoxib of 1:1 according to the invention, the endothermic sharp peak of the co-crystal corresponding to the melting point has an onset at 164° C.

Another embodiment of the present invention relates to a process for the production of a co-crystal according to the invention as described above comprising the steps of:
(a) dissolving or suspending an NSAID in a solvent; optionally heating the solution or dispersion to a temperature above ambient temperature and below the boiling point of the solution or dispersion;
(b) dissolving together with, or after, or before step (a) tramadol either as a free base or as a salt in a solvent,
(c) adding the solution of (b) to the solution of (a) and mixing them;
(d) cooling the mixed solution/dispersion of step (c) to ambient temperature;
(e) optionally evaporating part or all of the solvent; and
(f) filtering-off the resulting co-crystals.

Another embodiment of the present invention relates to a process for the production of a co-crystal according to the invention as described above comprising the steps of:
(a) dissolving or suspending an NSAID in a solvent; optionally heating the solution or dispersion to a temperature above ambient temperature and below the boiling point of the solution or dispersion;
(b) dissolving together with, or after, or before step (a) tramadol either as a free base or as a salt in a solvent, optionally combined with step (a) by dissolving tramadol already together with the NSAID in step (a)
(c) optionally adding the solution of (b) to the solution of (a) and mixing them;
(d) optionally adding a solvent to the solution of (a), (b) or (c) and mixing them;
(e) cooling the mixed solution/dispersion of step (a), (b), (c) or (d) to ambient temperature or below;
(f) optionally evaporating part or all of the solvent; and
(g) filtering-off the resulting co-crystals.

"Ambient temperature" is defined here as a temperature between 20 and 25° C., preferably being 20° C.

The solvents usable in these processes include water or organic solvents, preferably solvents selected from acetone, isobutyl acetate, acetonitrile, ethyl acetate, 2-butanol, dim- ethylcarbonate, chlorobenzene, butylether, diisopropylether, dimethylformamide, ethanol, water, hexane (also cyclohexane), isopropanol, methyl ethyl ketone (also methyl isobutylketone), methanol, methyl t-butyl ether, 3-pentanone, toluene and 1,1,1-trichloroethane, most preferably including alcohols, like ethanol. It is preferable—but not necessary—that the solvents in steps (a) and (c) are identical.

The molecular ratio between tramadol and the NSAID lies between 4:1 to 1:4, preferably from 3:1 to 1:3 and more preferably from 1:1 to 1:2.

Preferably the tramadol-solution in step (b) has a concentration of between 3M and 0.01 M.

The parts of the co-crystal according to the invention are well-known drugs with analgesic properties sometimes used for a long time worldwide. Due to this a further object of the present invention is a medicament comprising a co-crystal according to the invention.

Thus the invention also concerns a medicament comprising at least one co-crystal according to the invention as described above and optionally one or more pharmaceutically acceptable excipients.

The invention also relates to a pharmaceutical composition that comprises a therapeutically effective amount of the co-crystal according to the invention in a physiologically acceptable medium.

The association of two active principles in the same crystal exhibits several advantages. Being linked, they often behave as a single chemical entity, thus facilitating the treatments, formulation, dosage etc. In addition to that, with both tramadol and the NSAIDs being active analgesics these co-crystals are highly useful in the treatment of pain, especially also not losing any activity/weight by the addition of pharmacologically useless counterions as in salts with no API. In addition the two active principles are complementing each other in the treatment especially of pain, but possibly also of various other diseases or symptoms. Thus, the co-crystals according to the invention do combine a high number of advantages over the state of the art.

Another advantage is that the association of two active principles into one unique species seems to allow for a better Pharmacokinetic/Pharmacodynamic (PKPD) including also a better penetration of the blood-brain barrier, which helps in the treatment of pain.

In general, in most embodiments in which the co-crystals of tramadol are used (e.g. for the treatment of pain etc.), these co-crystals would be formulated into a convenient pharmaceutical formulation or a medicament. Accordingly, a desirable advantage of a co-crystal of tramadol, would show improved pharmaceutical properties and features, especially when compared to the free base or tramadol hydrochloride.

Thus, the co-crystal of tramadol according to the invention, should desirably show at least one, preferably more, of the following features:
to have a very small particle size, e.g. from 300 μm or lower; or
to be and/or remain essentially free of agglomerates; or
to be less or not very hygroscopic; or
to help in formulating controlled release or immediate release formulations; or
to have a high chemical stability; or
if given to a patient
to decrease the inter- and intra-subject variability in blood levels; or
to show a good absorption rate (e.g. increases in plasma levels or AUC); or
to show a high maximum plasma concentration (e.g. $C_{max}$); or to show decreased time to peak drug concentrations in plasma ($t_{max}$); or to show changes in half life of the compound ($t_{1/2}$), in whichever direction this change is preferably directed.

The medicament or pharmaceutical compositions according to the present invention may be in any form suitable for the application to humans and/or animals, preferably humans including infants, children and adults and can be produced by standard procedures known to those skilled in the art. The medicament of the present invention may for example be administered parenterally, including intramuscular, intraperitoneal, or intravenous injection, transmucosal or sublingual application; or orally, including administration as tablets, pellets, granules, capsules, lozenges, aqueous or oily solutions, suspensions, emulsions, sprays or as reconstituted dry powdered form with a liquid medium.

Typically, the medicaments according to the present invention may contain 1-60% by weight of one or more of the co-crystals as defined herein and 40-99% by weight of one or more auxiliary substances (additives/excipients).

The compositions of the present invention may also be administered topically or via a suppository.

The daily dosage for humans and animals may vary depending on factors that have their basis in the respective species or other factors, such as age, sex, weight or degree of illness and so forth. The daily dosage for humans preferably is in the range of 5 to 500 milligrams of tramadol to be administered during one or several intakes per day.

A further aspect of the invention relates to the use of co-crystal according to the invention as described above for the treatment of pain, preferably acute pain, chronic pain, neuropathic pain, hyperalgesia, allodynia or cancer pain, including diabetic neuropathy or osteoarthritis or fibromyalgia. A further aspect of the invention relates to the use of co-crystal according to the invention as described above for the treatment of pain, preferably acute pain, chronic pain, neuropathic pain, severe to moderate pain, hyperalgesia, allodynia or cancer pain, including diabetic neuropathy, osteoarthritis, fibromyalgia; rheumatoid arthritis, ankylosing spondylitis, frozen shoulder or sciatica. Preferably these uses are provided for in form of a medicament or a pharmaceutical composition according to the invention as described above.

Another object of the current invention is a method of treatment of pain, preferably acute pain, chronic pain, neuropathic pain, hyperalgesia, allodynia or cancer pain, including diabetic neuropathy or osteoarthritis or fibromyalgia, by providing to a patient in need thereof a sufficient amount of a co-crystal according to the invention as described above. Preferably the co-crystal according to the invention is provided in physiologically suitable form like e.g. in form of a medicament or a pharmaceutical composition according to the invention as described above.

The present invention is illustrated below with the help of the following figures and examples. These illustrations are given solely by way of example and do not limit the invention.

EXAMPLES

Example 1a

Process to Obtain (−)-Tramadol-(S)-Naproxen (1:2) Co-Crystal

Figure 1:
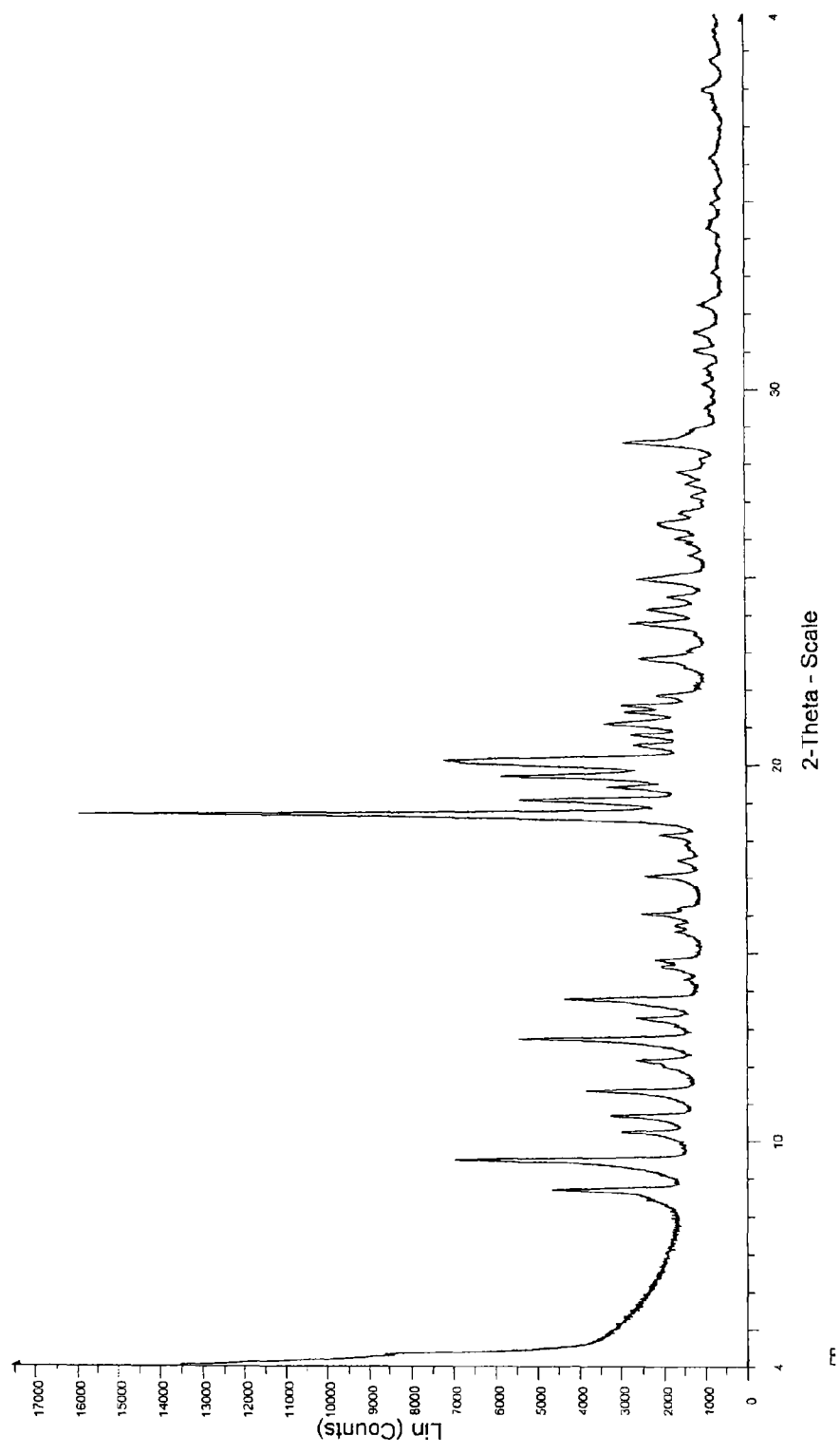
FIG. 1:
Powder X-Ray diffraction pattern of (−)-tramadol-(S)-naproxen 1:2 co-crystal.

A solution of (S)-naproxen (2.14 g, 9.3 mmol) in 20 mL of methanol was added in 10 minutes to a stirred solution of (−)-tramadol (2.45 g, 9.3 mmol) in 10 mL of methanol. The resulting solution was stirred at room temperature for 30 minutes and the solvent was evaporated under vacuum rendering a light yellow oil. The oil was cooled to −197° C. and allowed to warm to room temperature to give the amorphous (−)-tramadol-(S)-naproxen salt as a white solid (4.59 g, 100%).

Procedure:
The above obtained amorphous (−)-tramadol-(S)-naproxen salt (1:1) (2.2 g, 4.46 mmol) was suspended in 10 mL of diisopropyl ether and stirred for 7 days at room temperature. The resulting suspension was filtered off. The filtrate was washed with ca. 2 mL of diisopropyl ether and dried under vacuum at 40° C. (10 mm Hg) for 24 hours to give a co-crystal of (−)-tramadol-(S)-naproxen in a 1:2 ratio as a crystalline white solid (1.37 g, 85% yield referred to (S)-naproxen content of the initial mixture).

Example 1b

Process to Obtain (−)-Tramadol-(S)-Naproxen (1:2) Co-Crystal

A solution of (−)-tramadol (0.58 g, 2.20 mmol) in 2 mL of isopropanol was added to a stirred suspension of (S)-naproxen (1.02 g, 4.43 mmol, 2 eq) in 2 mL of isopropanol at 60° C. The resulting solution was cooled to room temperature and a third of the solvent was evaporated. The solution was seeded with 5-10 mg of crystalline (−)-tramadol-(S)-naproxen (1:2) co-crystal and was left standing at room temperature for 48 hours without stirring. The resulting suspension was filtered off, the filtrate was washed with ca. 1 mL of isopropanol and dried under vacuum (10 mm Hg) at 60° C. for 24 hours to give the co-crystal (−)-tramadol-(S)-naproxen in a 1:2 ratio as a white solid (1.31 g, 81%).

Characterisation of the Co-Crystal:

(−)-tramadol-(S)-naproxen (1:2) co-crystal obtained according to example 1 was fully characterised by $^1$H-NMR, FTIR, powder X-Ray diffraction, single crystal X-Ray diffraction, DSC and TG (see FIGS. 1 to 4).

The optical rotation value is $[\square]^{23}_D = +6°$ (c=1.00, MeOH) Powder X-Ray Diffraction (PXRD) Pattern of a Co-Crystal of (−)-Tramadol and (S)-Naproxen (1:2) (see FIG. 1).

Powder diffraction patterns were acquired on a D8 Advance Series 2Theta/Theta powder diffraction system using $Cu_{K\alpha}$-radiation in transmission geometry. The system is equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.4.1 and evaluation with EVA V.12.0 (see FIG. 1). The peaks expressed in angles $2\square$ and d-values are described in detail in table 1:

TABLE 1

List of selected peaks obtained by powder X-Ray diffraction of a co-crystal of (−)-tramadol and (S)-naproxen (1:2).

| Angle 2θ[1] | d-Value (Å) | Relative Intensity % |
| --- | --- | --- |
| 4.296 | 20.55171 | 8.9 |
| 8.659 | 10.20397 | 20.0 |
| 9.458 | 9.34300 | 36.6 |
| 10.209 | 8.65740 | 10.4 |
| 10.634 | 8.31301 | 12.5 |
| 11.302 | 7.82251 | 16.4 |
| 12.118 | 7.29783 | 9.3 |
| 12.693 | 6.96824 | 28.2 |
| 13.241 | 6.68136 | 9.4 |
| 13.754 | 6.43322 | 21.3 |
| 14.278 | 6.19841 | 2.4 |
| 14.626 | 6.05175 | 6.3 |
| 14.790 | 5.98498 | 7.3 |
| 15.551 | 5.69362 | 4.3 |
| 15.711 | 5.63613 | 4.3 |
| 16.015 | 5.52985 | 9.6 |
| 16.176 | 5.47506 | 4.0 |
| 17.033 | 5.20140 | 9.1 |
| 17.449 | 5.07826 | 4.2 |
| 17.882 | 4.95625 | 3.1 |
| 18.131 | 4.88881 | 7.3 |
| 18.700 | 4.74132 | 100.0 |
| 19.060 | 4.65259 | 29.6 |
| 19.407 | 4.57012 | 15.7 |
| 19.705 | 4.50167 | 32.7 |
| 20.115 | 4.41077 | 41.6 |
| 20.525 | 4.32376 | 11.6 |
| 20.795 | 4.26805 | 12.1 |
| 21.097 | 4.20773 | 16.5 |
| 21.409 | 4.14714 | 13.2 |
| 21.579 | 4.11476 | 13.8 |
| 21.855 | 4.06355 | 8.4 |

[1]The 2θ values were obtained using cupper radiation ($Cu_{K\alpha}$ 1.54060 Å)

$^1$H-NMR Spectrum of a Co-Crystal of (−)-Tramadol and (S)-Naproxen (1:2):

Proton nuclear magnetic resonance analyses were recorded in deuterated methanol (MeOH-d4) in a Bruker Avance 400 Ultrashield NMR spectrometer, equipped with a z-gradient 5 mm BBO (Broadband Observe) probe. Spectra were acquired solving 2-10 mg of sample in 0.6 mL of deuterated solvent.

$^1$H NMR spectrum (in d4-methanol at 400 MHz) δ shows peaks at 1.47-1.96 (m, 8H), 1.51 (d, J=7 Hz, 6H), 2.17 (m, 1H), 2.55 (dd, J=2 Hz, J=13 Hz, 1H), 2.57 (s, 6H), 2.88 (dd, J=9 Hz, J=13 Hz, 1H), 3.78 (q, J=7 Hz, 2H), 3.80 (s, 3H), 3.89 (s, 6H), 6.82 (dd, J=2 Hz, J=8 Hz, 1H), 7.07 (m, 4H), 7.19 (d, J=2 Hz, 2H), 7.29 (t, J=8 Hz, 1H), 7.45 (dd, J=2 Hz, J=8 Hz, 2H), 7.70 (m, 6H).

FT-IR Spectrum of a Co-Crystal of (−)-Tramadol and (S)-Naproxen (1:2):

The FTIR spectra (ATR) of the co-crystal of (−)-tramadol-(S)-naproxen were recorded using a Bruker Tensor 27, equipped with a MKII golden gate single reflection ATR system, a mid-infrared source as the excitation source and a DTGS detector. The spectra were acquired in 32 scans at a resolution of 4 cm$^{-1}$.

The sample of (−)-tramadol-(S)-naproxen co-crystal (1:2) shows a Fourier Transform Infra Red spectrum (ATR) with absorption bands $\upsilon_{max}$ at 3247, 2942, 1699, 1633, 1605, 1583, 1485, 1380, 1271, 1223, 1160, 1029, 851, 789 and 704 cm$^{-1}$.

DSC Analysis of a Co-Crystal of (−)-Tramadol and (S)-Naproxen (1:2) (See FIG. 2):

DSC analyses were recorded in a Mettler Toledo DSC822e. Samples of 1-2 mg were weighted into 40 μL aluminium crucibles with a pinhole lid, and were heated, under nitrogen (50 mL/min), at 10° C./min from 30 to 300° C.

Figure 2:
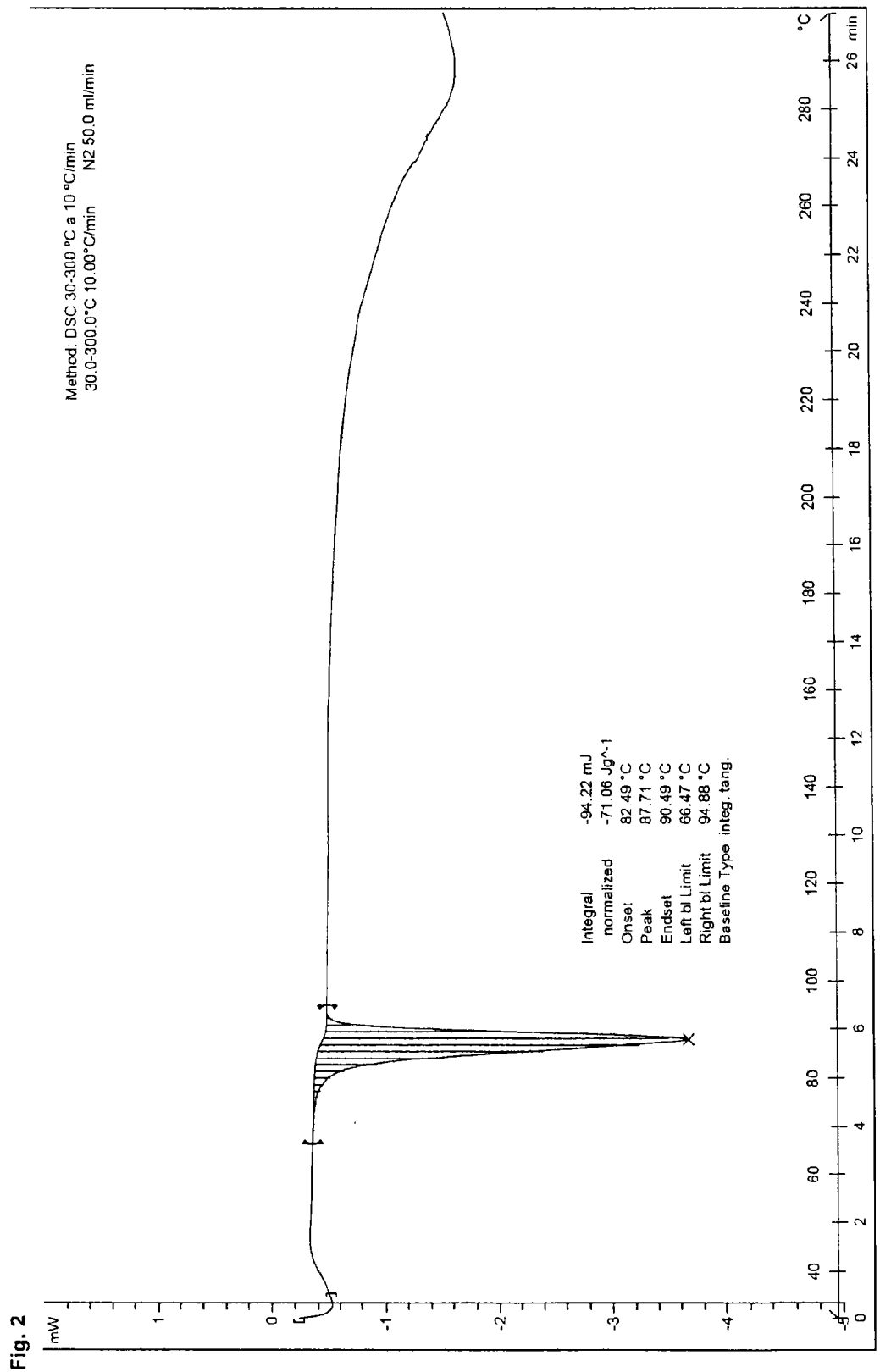
FIG. 2:
DSC analysis of (−)-tramadol-(S)-naproxen 1:2 co-crystal.

The endothermic peak of the DSC analysis of (−)-tramadol-(S)-naproxen co-crystal (1:2) corresponds to the melting point with an onset at 82° C., see FIG. 2.

TG Analysis of a Co-Crystal of (−)-Tramadol and (S)-Naproxen (1:2) (See FIG. 3):

Thermogravimetric analyses were recorded in a Mettler Toledo SDTA851e. Samples of 3-4 mg were weighted into 40 μL aluminium crucibles with a pinhole lid, and heated at 10° C./min from 30 to 500° C., under nitrogen (80 mL/min).

Figure 3:
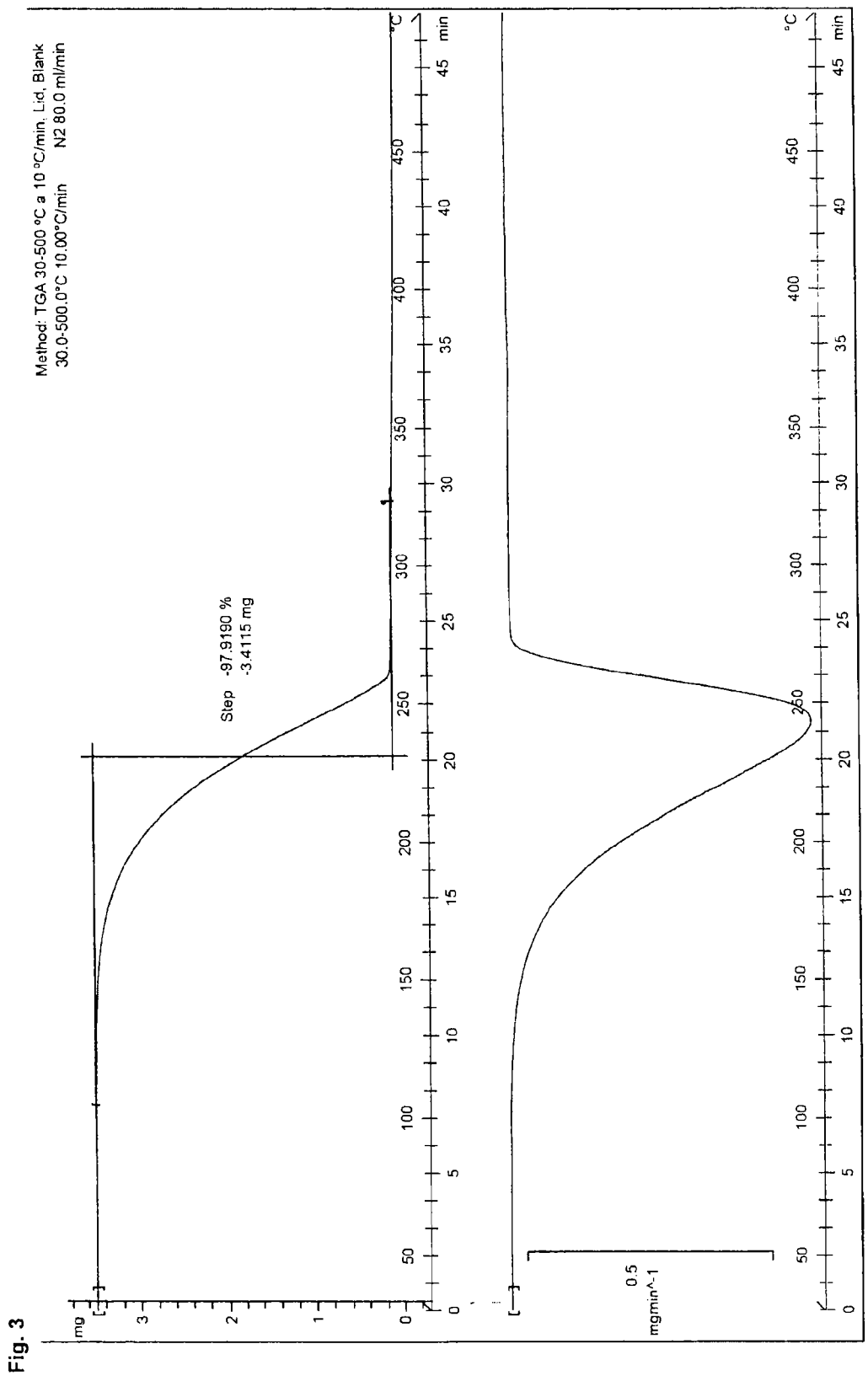
FIG. 3:
TG analysis of (−)-tramadol-(S)-naproxen 1:2 co-crystal.

The TG analysis of the (−)-tramadol-(S)-naproxen co-crystal (1:2) according to the invention does not show weight loss at temperatures below the melting point (see FIG. 3).

Figure 4:
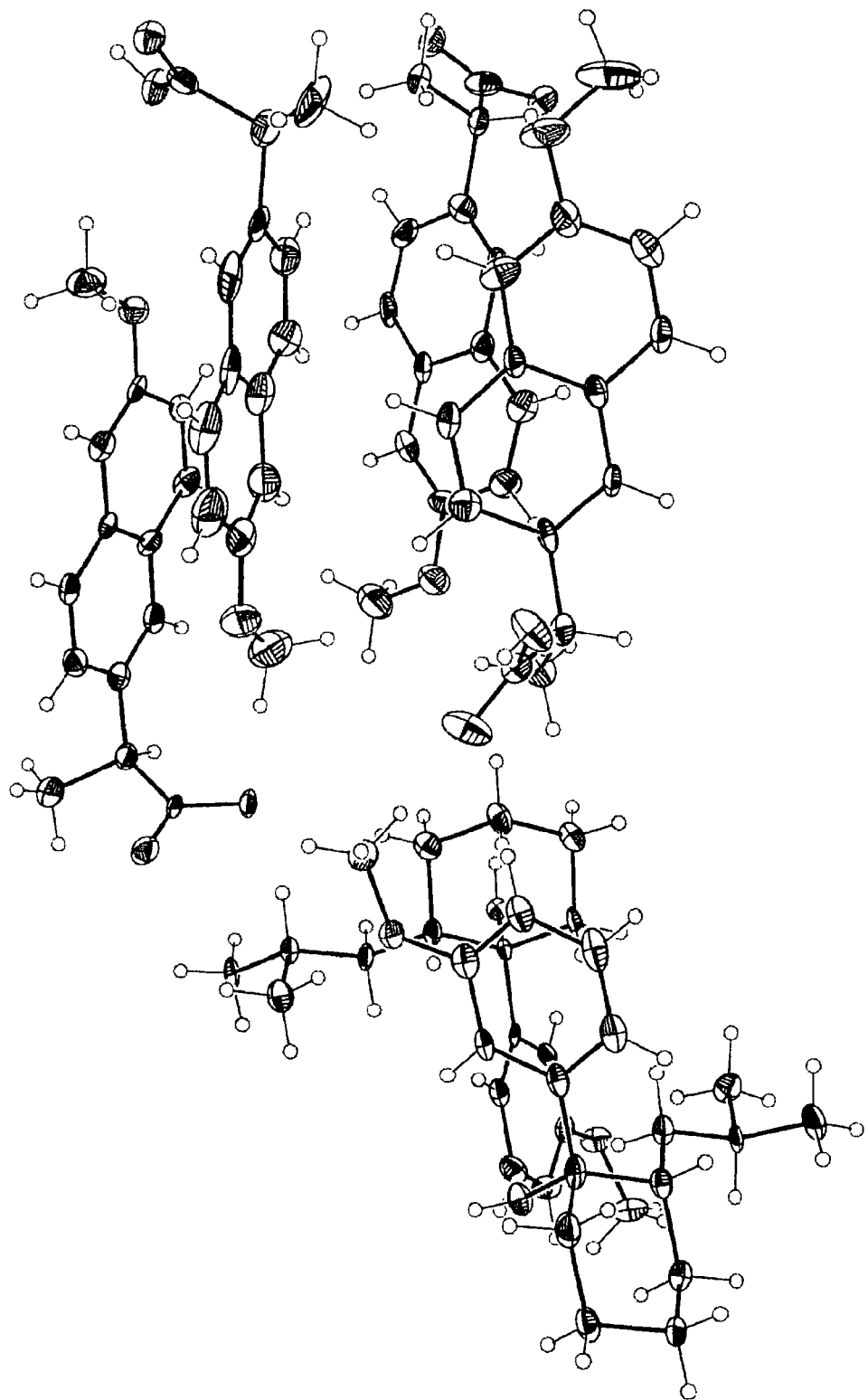
FIG. 4:
Structure of the unit cell of the (−)-tramadol-(S)-naproxen 1:2 co-crystal obtained by SCXRD analysis showing four molecules of (S)-naproxen and two molecules of (−)-tramadol.
Figure 5:
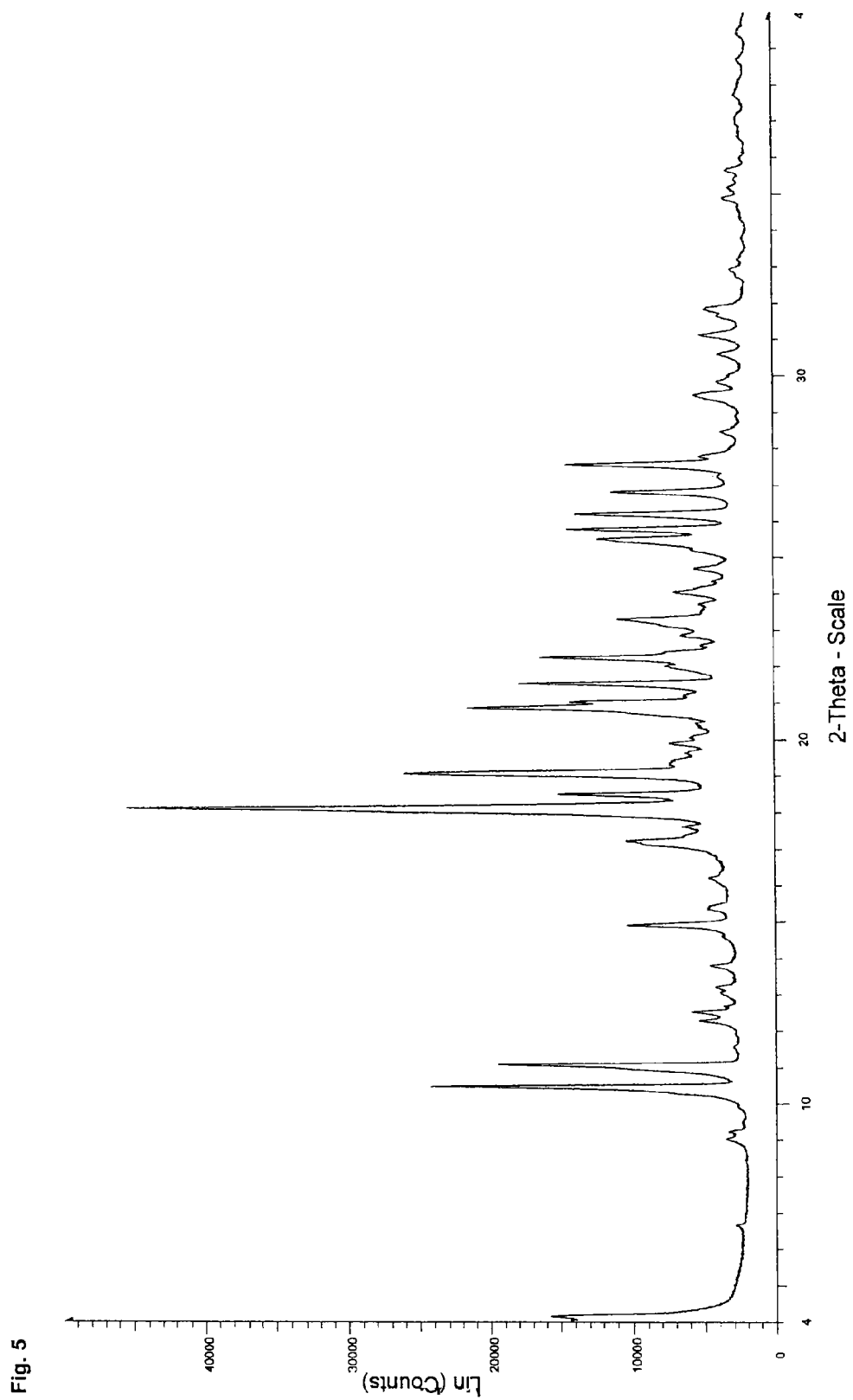
FIG. 5:
Powder X-Ray diffraction pattern of the (+)-tramadol-(R)-naproxen 1:2 methanol solvate co-crystal.
Figure 6:
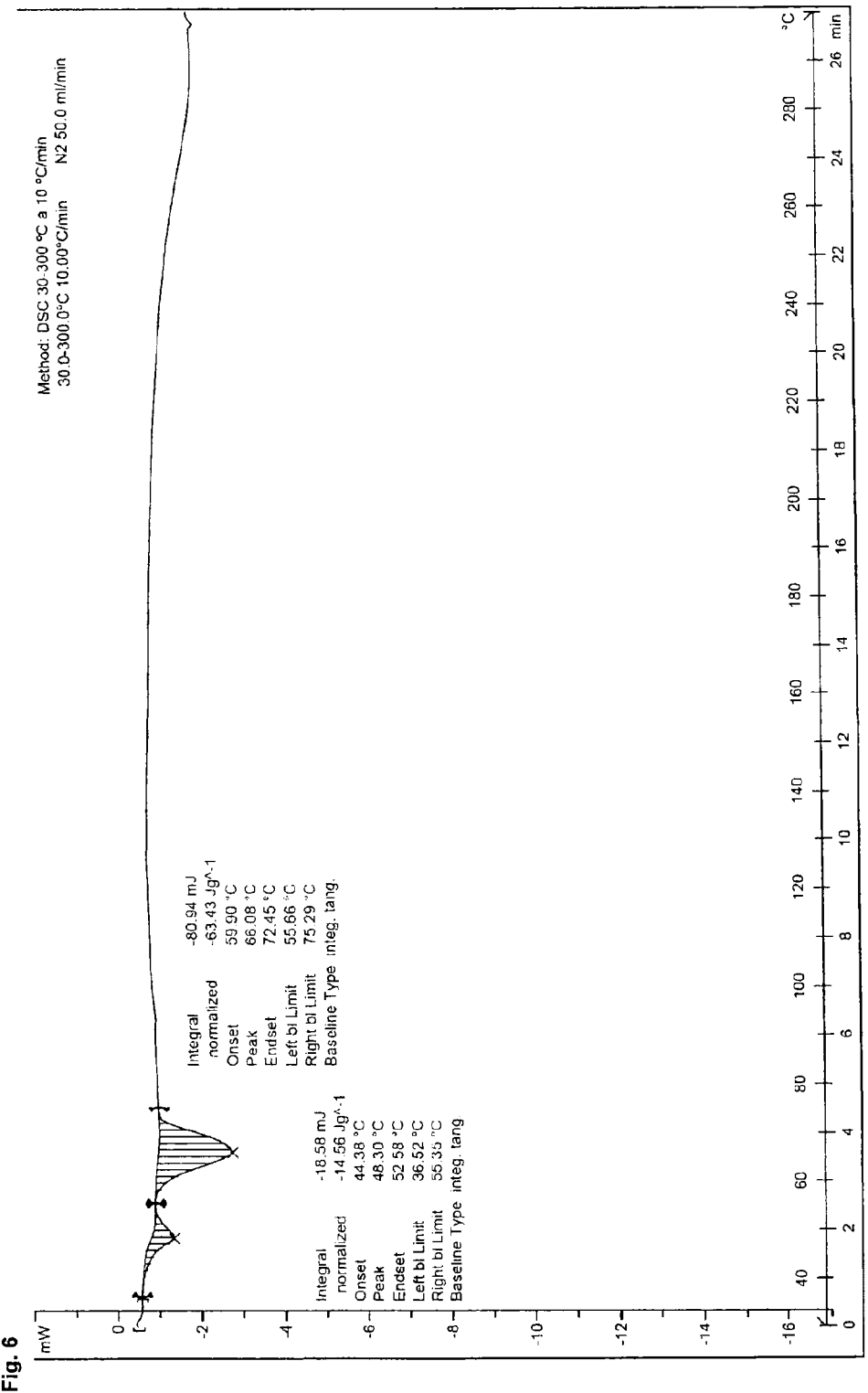
FIG. 6:
DSC analysis of (+)-tramadol-(R)-naproxen 1:2 methanol solvate co-crystal.
Figure 7:
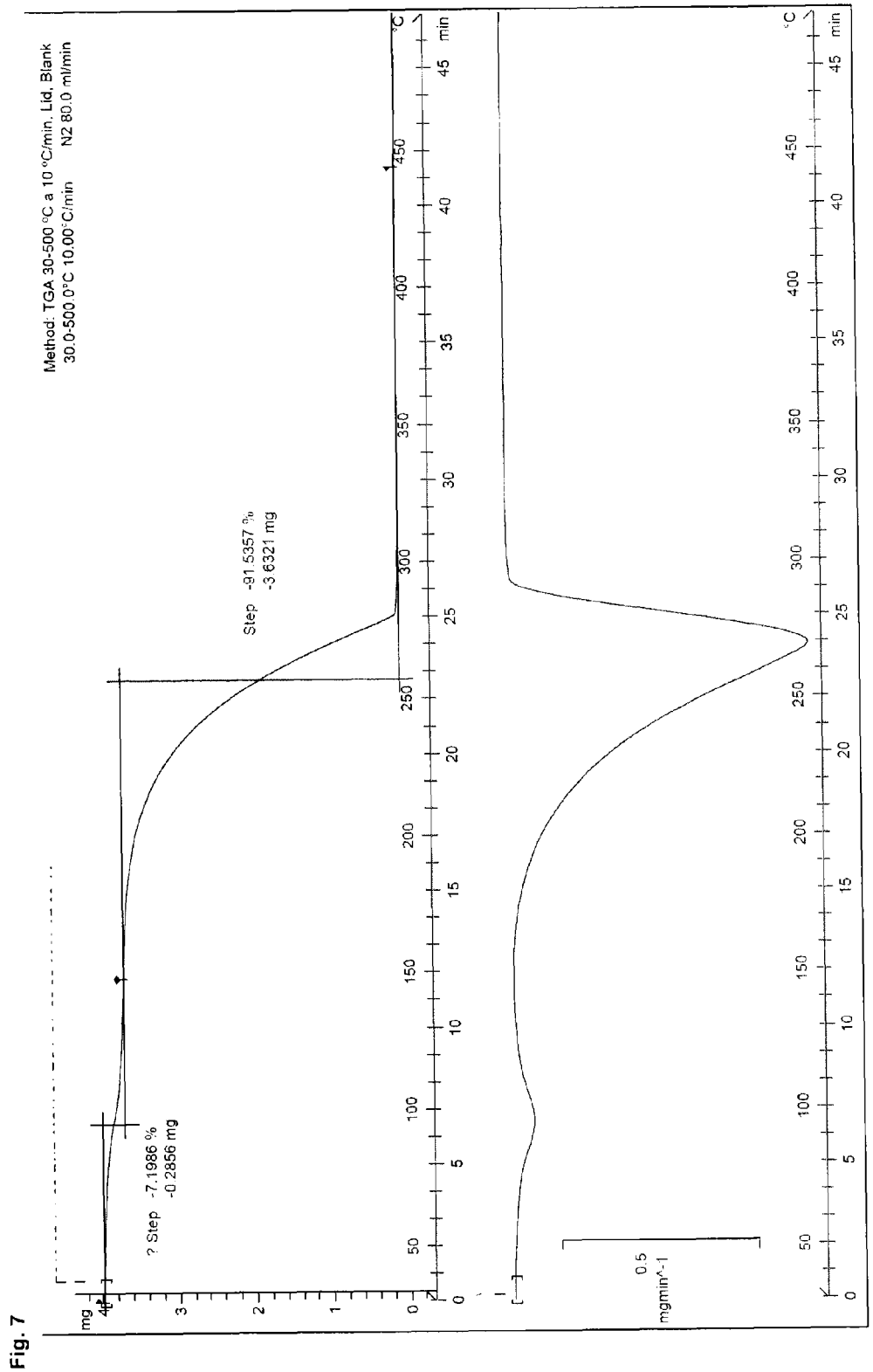
FIG. 7:
TG analysis of the (+)-tramadol-(R)-naproxen 1:2 methanol solvate co-crystal.

Single Crystal XRD Analysis of a Single Crystal of a Co-Crystal of (−)-Tramadol and (S)-Naproxen (1:2) (See FIG. 4):

The crystal structure was determined from single crystal X-ray diffraction data. The measured crystal obtained from the preparation according to example 1 was selected using a Zeiss stereomicroscope using polarized light and prepared under inert conditions immersed in perfluoropolyether as protecting oil for manipulation. Crystal structure determination was carried out using a Bruker-Nonius diffractometer equipped with a APPEX 2 4K CCD area detector, a FR591 rotating anode with $Mo_{K\alpha}$ radiation, Montel mirrors as monochromator and a Kryoflex low temperature device (T=100 K). Fullsphere data collection omega and phi scans. Programs used: Data collection Apex2 V. 1.0-22 (Bruker-Nonius 2004), data reduction Saint+Version 6.22 (Bruker-Nonius 2001) and absorption correction SADABS V. 2.10 (2003). Crystal structure solution was achieved using direct methods as implemented in SHELXTL Version 6.10 (Sheldrick, Universität Göttingen (Germany), 2000) and visualized using XP program. Missing atoms were subsequently located from difference Fourier synthesis and added to the atom list. Least-squares refinement on $F_0^2$ using all measured intensities was carried out using the program SHELXTL Version 6.10 (Sheldrick, Universität Göttingen (Germany), 2000). All non hydrogen atoms were refined including anisotropic displacement parameters. In FIG. 4 the structure of the co-crystal is shown. Crystal data and structure refinement for (−)-tramadol-(S)-naproxen (1:2) co-crystal is given in the following table 2.

TABLE 2

Most relevant structural data of the SCXRD analysis of a co-crystal of (−)-tramadol-(S)-naproxen (1:2).

| Crystal system | Monoclinic |
|---|---|
| Space group: | P2$_1$ |
| A (Å) | 9.512(2) |
| B (Å) | 40.5736(11) |
| C (Å) | 10.323(4) |
| α (°) | 90 |
| β (°) | 96.29(1) |
| γ (°) | 90 |
| Z | 2 |
| Volume (Å$^3$) | 3959.9(16) |

Example 2

(+)-Tramadol-(R)-Naproxen (1:2) Co-Crystal

Process to Obtain (+)-Tramadol-(R)-Naproxen (1:2) Co-Crystal:

A solution of (R)-naproxen (751 mg, 3.26 mmol) in 4 mL of methanol was added to a solution of (+)-tramadol (430 mg, 1.63 mmol) in 1 mL of methanol. The mixture was stirred for 30 minutes and the solvent was evaporated under vacuum rendering an oil, which solidified by cooling to −197° C. The resulting solid was suspended in 10 mL of diisopropyl ether and stirred for 7 days at room temperature. The resulting suspension was filtered off. The filtrate was washed with 5 mL of diisopropyl ether and dried under vacuum at 40° C. (10 mm Hg) for 16 hours to give a co-crystal of (+)-tramadol-(R)-naproxen in a 1:2 ratio as a crystalline white solid (620 mg, 53%).

Characterisation of the Co-Crystal:

(+)-tramadol-(R)-naproxen (1:2) co-crystal obtained according to example 2 was fully characterised by $^1$H-NMR, FTIR, powder X-Ray diffraction, DSC and TG.

All the data obtained were identical to the data obtained for its enantiomer (−)-tramadol-(S)-naproxen (1:2) co-crystal of Example 1, the only difference being the optical rotation value of [□]$^{23}_D$=−7° (c=1.00, MeOH) and DSC (10° C./min): endothermic peak corresponding to the melting point with an onset at 84° C.

Example 3

(+)-Tramadol-(R)-Naproxen (1:2) Methanol Solvate Co-Crystal

Process to Obtain (+)-Tramadol-(R)-Naproxen (1:2) Methanol Solvate Co-Crystal:

A solution of (R)-naproxen (925 mg, 4.02 mmol) in 3 mL of methanol was added to a solution of (+)-tramadol (530 mg, 2.01 mmol) in 1 mL of methanol. The mixture was stirred for 10 minutes and about half of the solvent was evaporated. The resulting solution was left standing at room temperature and after 24 hours a solid had formed. The solid was filtered off, the filtrate was washed with 2 mL of methanol and dried under vacuum (10 mm Hg) for 4 hours to give the methanol solvate of the 1:2 co-crystal of (+)-tramadol-(R)-naproxen as crystalline white needles (610 mg, 42%).

Characterisation of the Co-Crystal:

(+)-tramadol-(R)-naproxen (1:2) methanol solvate co-crystal obtained according to example 3 was fully characterised by $^1$H-NMR, FTIR, powder X-Ray diffraction, DSC and TG (see FIGS. 5 to 8).

The optical rotation value is [α]$^{23}_D$=−5° (c=1.00, MeOH).

Powder X-Ray Diffraction (PXRD) Pattern of a (+)-Tramadol-(R)-Naproxen Methanol Solvate (1:2) Co-Crystal (See FIG. 5):

Powder diffraction patterns were acquired on a D8 Advance Series 2Theta/Theta powder diffraction system using Cu$_{K\alpha}$-radiation in transmission geometry. The system is equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.4.1 and evaluation with EVA V.12.0 (see FIG. 5). The peaks expressed in angles 2θ and d-values are described in detail in table 3:

TABLE 3

List of selected peaks obtained by powder X-Ray diffraction of (+)-tramadol-(R)-naproxen methanol solvate (1:2) co-crystal.

| Angle 2θ[1] | d-Value (Å) | Relative Intensity % |
|---|---|---|
| 4.118 | 21.44081 | 12.1 |
| 6.606 | 13.37037 | 1.4 |
| 9.002 | 9.81544 | 3.7 |
| 9.190 | 9.61534 | 3.2 |
| 10.447 | 8.46109 | 49.5 |
| 11.043 | 8.00578 | 39.3 |
| 11.547 | 7.65723 | 2.5 |
| 12.266 | 7.21033 | 7.8 |
| 12.498 | 7.07682 | 8.9 |
| 12.671 | 6.98047 | 4.1 |
| 13.041 | 6.78342 | 4.6 |
| 13.191 | 6.70672 | 5.3 |
| 13.778 | 6.42196 | 6.0 |
| 14.907 | 5.93807 | 19.4 |
| 15.384 | 5.75499 | 6.6 |
| 16.195 | 5.46846 | 6.3 |
| 17.204 | 5.15004 | 19.0 |
| 17.610 | 5.03216 | 10.4 |
| 18.124 | 4.89075 | 100.0 |
| 18.499 | 4.79232 | 30.4 |
| 19.080 | 4.64786 | 55.8 |
| 19.352 | 4.58308 | 12.5 |
| 19.643 | 4.51573 | 9.8 |
| 19.898 | 4.45840 | 12.6 |
| 20.074 | 4.41971 | 9.0 |
| 20.424 | 4.34491 | 8.3 |
| 20.881 | 4.25078 | 45.4 |
| 21.035 | 4.22003 | 28.5 |
| 21.552 | 4.11988 | 36.9 |
| 22.023 | 4.03290 | 13.3 |
| 22.263 | 3.98986 | 33.4 |
| 22.580 | 3.93462 | 7.6 |

[1]The 2θ values were obtained using cupper radiation (Cu$_{K\alpha}$ 1.54060 Å)

$^1$H-NMR Spectrum of a (+)-Tramadol-(R)-Naproxen Methanol Solvate (1:2) Co-Crystal:

Proton nuclear magnetic resonance analyses were recorded in deuterated methanol (MeOH-d4) in a Bruker Avance 400 Ultrashield NMR spectrometer, equipped with a z-gradient 5 mm BBO (Broadband Observe) probe. Spectra were acquired solving 2-10 mg of sample in 0.6 mL of deuterated solvent. $^1$H NMR spectrum (in d4-methanol at 400 MHz) δ shows peaks at 1.41-1.93 (m, 8H), 1.51 (d, J=7 Hz, 6H), 2.13 (m, 1H), 2.52 (m, 7H), 2.87 (dd, J=9 Hz, J=13 Hz, 1H), 3.35 (2×MeOH), 3.77 (q, J=7 Hz, 2H), 3.79 (s, 3H), 3.88 (s, 6H), 6.81 (dd, J=2 Hz, J=8 Hz, 1H), 7.02 (d, J=7 Hz, 1H), 7.09 (m, 3H), 7.18 (d, J=2 Hz, 2H), 7.27 (t, J=8 Hz, 1H), 7.45 (dd, J=1 Hz, J=8 Hz, 2H), 7.66-7.74 (m, 6H).

FT-IR Spectrum of a (+)-Tramadol-(R)-Naproxen Methanol Solvate (1:2) Co-Crystal:

The FTIR spectra (ATR) of the (+)-tramadol-(R)-naproxen methanol solvate (1:2) co-crystal were recorded using a Bruker Tensor 27, equipped with a MKII golden gate single reflection ATR system, a mid-infrared source as the excitation source and a DTGS detector. The spectra were acquired in 32 scans at a resolution of 4 cm$^{-1}$. The sample of (+)-tramadol-(R)-naproxen methanol solvate (1:2) co-crystal shows a Fourier Transform Infra Red spectrum (ATR) with absorption bands $\upsilon_{max}$ at 3523, 3151, 2928, 2861, 2465, 1706, 1632, 1603, 1567, 1485, 1461, 1445, 1417, 1388 and 1362 cm$^{-1}$.

DSC analysis of a (+)-tramadol-(R)-naproxen methanol solvate (1:2) co-crystal (see FIG. 6):

DSC Analyses were Recorded in a Mettler Toledo DSC822e. Samples of 1-2 mg were weighted into 40 μL aluminium crucibles with a pinhole lid, and were heated, under nitrogen (50 mL/min), at 10° C./min from 30 to 300° C. The endothermic peaks of the (+)-tramadol-(R)-naproxen methanol solvate co-crystal (1:2) measured had onsets at 44° C. and 60° C., see FIG. 6.

TG Analysis of a Co-Crystal of (+)-Tramadol-(R)-Naproxen Methanol Solvate (1:2) Co-Crystal (See FIG. 7):

Thermogravimetric analyses were recorded in a Mettler Toledo SDTA851e. Samples of 3-4 mg were weighted into 40 μL aluminium crucibles with a pinhole lid, and heated at 10° C./min from 30 to 500° C., under nitrogen (80 mL/min). The TG analysis of the (+)-tramadol-(R)-naproxen methanol solvate (1:2) co-crystal according to the invention does show weight loss of 7.2% between 40 and 140° C. followed by decomposition starting at 160° C. (see FIG. 7).

Example 4

(Rac)-Tramadol.HCl-Celecoxib (1:1) Co-Crystal

Process to Obtain (Rac)-Tramadol.HCl-Celecoxib (1:1) Co-Crystal:

Example 4a

Preparation Via Solvent-Assisted Grinding

A 5 mL stainless steel ball-mill reactor was charged with two 7 mm steel balls, (rac)-tramadol hydrochloride (48 mg, 0.16 mmol), celecoxib (61 mg, 0.16 mmol, 1 eq) and 1 drop of methyl isobutyl ketone. The reactor was agitated at 30 Hz for 45 minutes. Traces of solvent were removed in vacuo affording (rac)-tramadol.HCl-celecoxib (1:1) co-crystal as a white solid (109 mg, quantitative yield).

Example 4b

Large Scale Via Crystallization

To a 1 L three necked flask equipped with mechanical stirrer, addition funnel and cooler containing tramadol.HCl (26.54 g, 88.5 mmol) and celecoxib (33.74 g, 88.5 mmol, 1 eq.), was added 122 mL ethanol. The resultant suspension was heated to reflux (complete dissolution). Cyclohexane (203 mL) was added slowly to the solution maintaining the reflux (addition time 20 min) and then, the solution was cooled slowly to room temperature with stirring. The solution was seeded at 55° C. with form obtained in Example 4a and the crystallization started). The mixture was cooled 2 h at 0° C.

The white solid was filtered with a sintered funnel n° 3 and washed with a solvent mixture at 0-5° C. (1 vol., 60 mL, (0.6:1) EtOH/cyclohexane). After drying 2 days at room temperature under vacuum, (rac)-tramadol.HCl-celecoxib (1:1) co-crystal was obtained as a white solid (54.6 g, 91% yield).

Figure 8:
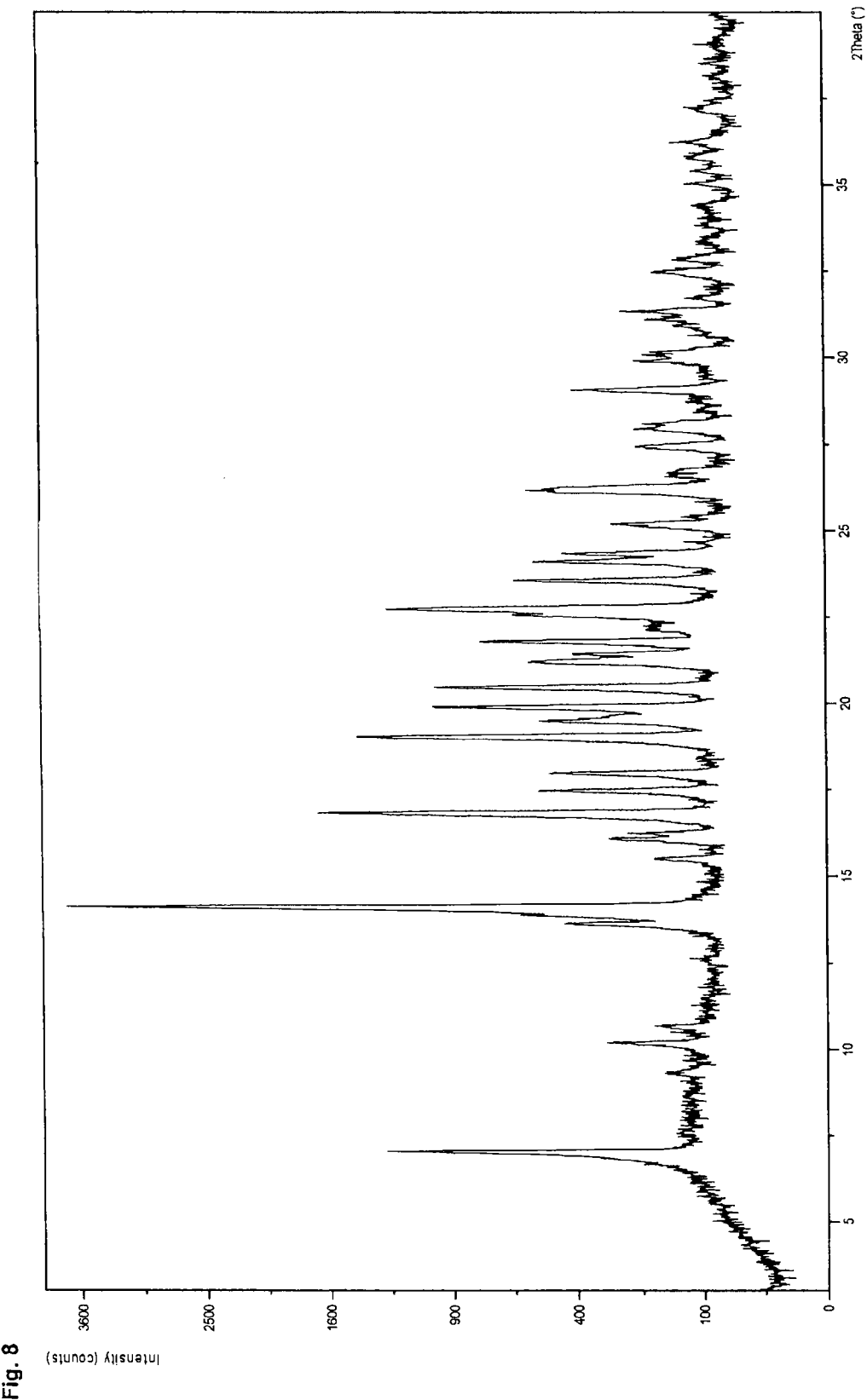
FIG. 8:
Powder X-Ray diffraction pattern of the (rac)-tramadol.HCl-celecoxib 1:1 co-crystal.
Figure 9:
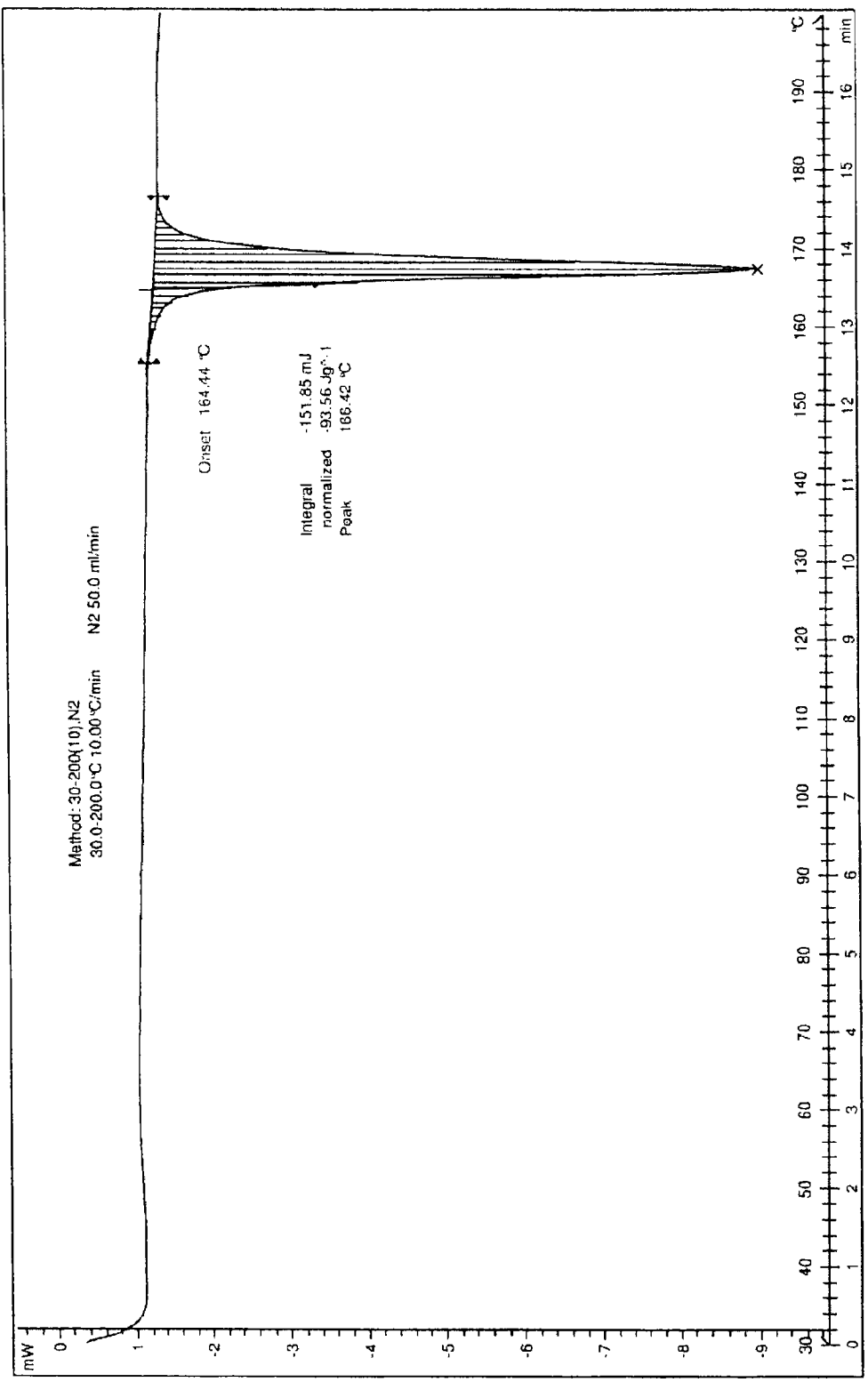
FIG. 9:
DSC analysis of the (rac)-tramadol.HCl-celecoxib 1:1 co-crystal.
Figure 10:
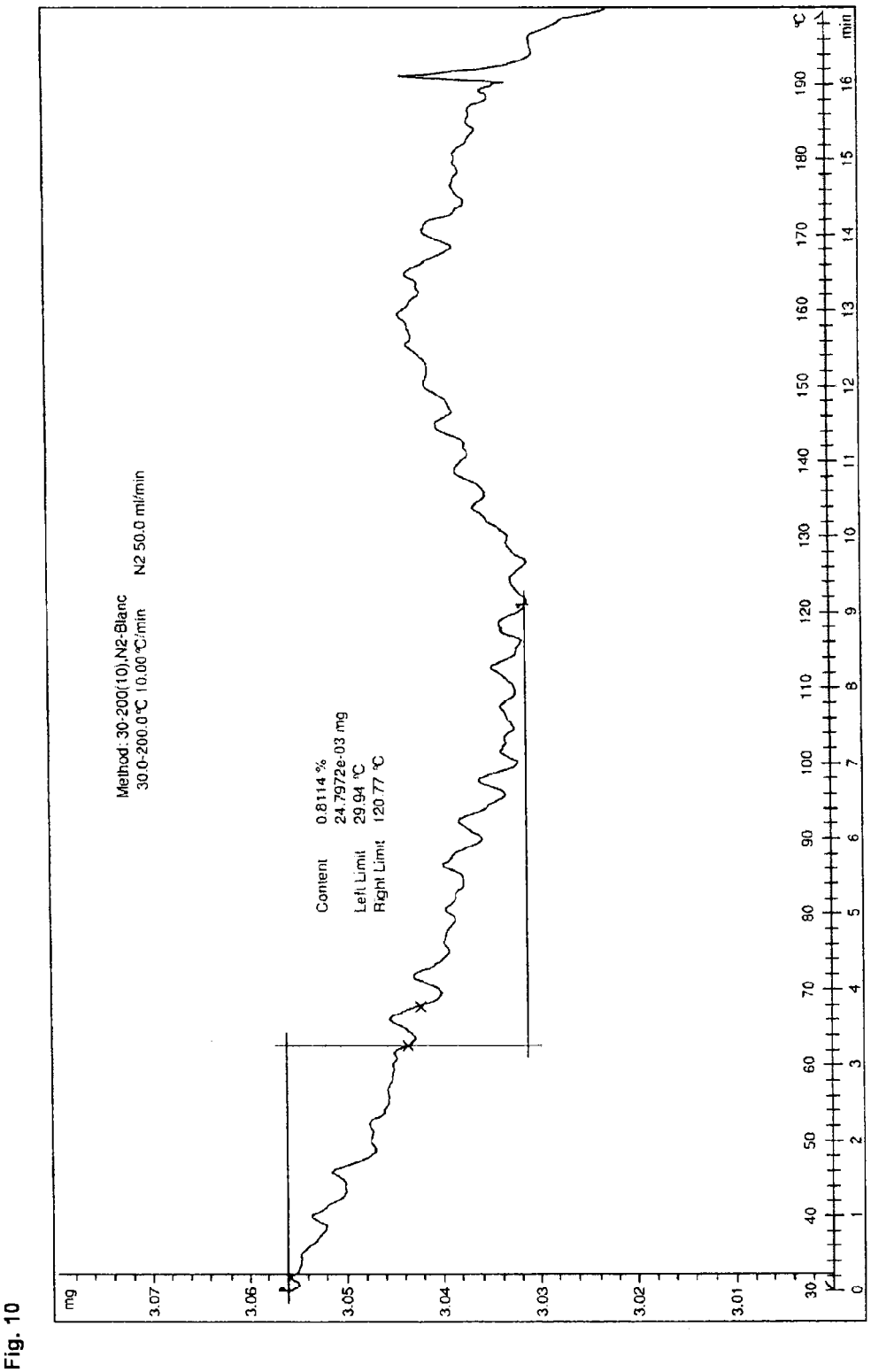
FIG. 10:
TG analysis of the (rac)-tramadol.HCl-celecoxib 1:1 co-crystal.

Characterisation of the Co-Crystal:

(rac)-tramadol.HCl-celecoxib (1:1) co-crystal obtained according to example 4 was fully characterised by $^1$H-NMR, FTIR, powder X-Ray diffraction, DSC and TG (see FIGS. 8 to 10).

Powder X-Ray Diffraction (PXRD) Pattern of a (Rac)-Tramadol.HCl-Celecoxib (1:1) Co-Crystal: (See FIG. 8):

PXRD analysis was performed using a Philips X'Pert diffractometer with Cu K$_\alpha$ radiation in Bragg-Brentano geometry. The system is equipped with a monodimensional, real time multiple strip detector. The measurement parameters were as follows: the range of 2θ was 3° to 40° at a scan rate of 8.8° per minute (see FIG. 8). The peaks expressed in angles 2θ and d-values are described in detail in table 4:

TABLE 4

List of selected peaks obtained by powder X-Ray diffraction of (rac)-tramadol•HCl - celecoxib (1:1) co-crystal.

| Angle 2θ[1] | d-Value (Å) | Relative Intensity % |
|---|---|---|
| 7.06 | 12.52 | 29 |
| 9.32 | 9.49 | 1 |
| 10.21 | 8.67 | 5 |
| 10.69 | 8.27 | 2 |
| 13.64 | 6.49 | 10 |
| 13.86 | 6.39 | 14 |
| 14.13 | 6.27 | 100 |
| 15.53 | 5.71 | 3 |
| 16.10 | 5.51 | 6 |
| 16.25 | 5.45 | 5 |
| 16.85 | 5.26 | 44 |
| 17.50 | 5.07 | 12 |
| 18.00 | 4.93 | 11 |
| 19.05 | 4.66 | 38 |
| 19.48 | 4.56 | 11 |
| 19.91 | 4.46 | 25 |
| 20.48 | 4.34 | 25 |
| 21.18 | 4.19 | 11 |
| 21.27 | 4.18 | 11 |
| 21.44 | 4.14 | 8 |
| 21.80 | 4.08 | 18 |
| 22.14 | 4.02 | 3 |
| 22.56 | 3.94 | 14 |
| 22.73 | 3.91 | 32 |
| 23.57 | 3.78 | 15 |
| 24.11 | 3.69 | 13 |
| 24.36 | 3.65 | 10 |
| 25.20 | 3.53 | 6 |
| 26.12 | 3.41 | 11 |
| 26.58 | 3.35 | 2 |
| 26.77 | 3.33 | 2 |
| 27.45 | 3.25 | 5 |
| 27.94 | 3.19 | 4 |
| 28.13 | 3.17 | 3 |
| 29.07 | 3.07 | 9 |
| 29.91 | 2.99 | 3 |
| 30.15 | 2.96 | 3 |
| 31.11 | 2.88 | 3 |
| 31.34 | 2.85 | 5 |
| 31.74 | 2.82 | 1 |
| 32.49 | 2.76 | 3 |
| 32.83 | 2.73 | 2 |
| 34.42 | 2.61 | 1 |
| 35.04 | 2.56 | 2 |
| 35.76 | 2.51 | 1 |
| 36.24 | 2.48 | 2 |
| 37.19 | 2.42 | 1 |

[1]The 2θ values were obtained using cupper radiation (Cu$_{K\alpha}$ 1.54060 Å)

$^1$H-NMR Spectrum of a Co-Crystal of (Rac)-Tramadol.HCl and Celecoxib (1:1):

Proton nuclear magnetic resonance analyses were recorded in methanol-d$_4$ in a Varian Mercury 400 spectrometer, equipped with a broadband probe ATB 1H/19F/X of 5 mm. Spectra were acquired dissolving 5-10 mg of sample in 0.6 mL of deuterated solvent.

¹H NMR spectrum (in d4-methanol at 400 MHz) δ shows peaks at 7.97-7.90 (m, 2H); 7.53-7.46 (m, 2H); 7.30 (t, J=8.0 Hz, 1H); 7.22-7.14 (m, 4H); 7.12-7.09 (m, 1H); 7.07 (d, J=7.8 Hz, 1H); 6.90 (s, 1H); 6.83 (dd, J=2.7 Hz, J=8.2 Hz, 1H); 3.80 (s, 3H); 2.98 (dd, J=9.0 Hz, J=13.3 Hz, 1H); 2.75-2.60 (m, 8H); 2.35 (s, 3H); 2.28-2.18 (m, 1H); 2.00-1.46 (m, 8H) ppm.
FT-IR Spectrum of a Co-Crystal of (Rac)-Tramadol.HCl and Celecoxib (1:1):

FTIR spectra were recorded using a Thermo Nicolet Nexus 870 FT-IR, equipped with a beamsplitter KBr system, a 35 mW He—Ne laser as the excitation source and a DTGS KBr detector. The spectra were acquired in 32 scans at a resolution of 4 cm⁻¹.

The sample (KBr pellet) shows a Fourier Transform Infra Red spectrum with absorption bands at 3481.6 (m), 3133.5 (m), 2923.0 (m), 2667.7 (m), 1596.0 (m), 1472.4 (m), 1458.0 (m), 1335.1 (m), 1288.7 (m), 1271.8 (m), 1168.7 (s), 1237.3 (m), 1168.7 (s), 1122.6 (s), 1100.9 (m), 1042.2 (m), 976.8 (m), 844.6 (m), 820.1 (m), 786.5 (m) 625.9 (m) cm⁻¹.
DSC Analysis of a Co-Crystal of (Rac)-Tramadol.HCl and Celecoxib (1:1) (See FIG. 9):

DSC analyses were recorded with a Mettler DSC822$^e$. A sample of 1.6230 mg was weighed into 40 μL aluminium crucible with a pinhole lid and was heated, under nitrogen (50 mL/min), at 10° C./min from 30 to 200° C.

The novel type of crystal of the present invention is characterized in that the endothermic sharp peak corresponding to the melting point has an onset at 164.44° C. (fusion enthalpy −93.56 J/g), measured by DSC analysis (10° C./min) (see FIG. 9).
TG Analysis of a Co-Crystal of (Rac)-Tramadol.HCl and Celecoxib (1:1) (See FIG. 10):

Thermogravimetric analyses were recorded in a thermogravimetric analyzer Mettler TGA/SDTA851$^e$. A sample of 3.0560 mg was weighed into a 70 μL alumina crucible with a pinhole lid and was heated at 10° C./min from 30 to 200° C., under nitrogen (50 mL/min).

Figure 11:
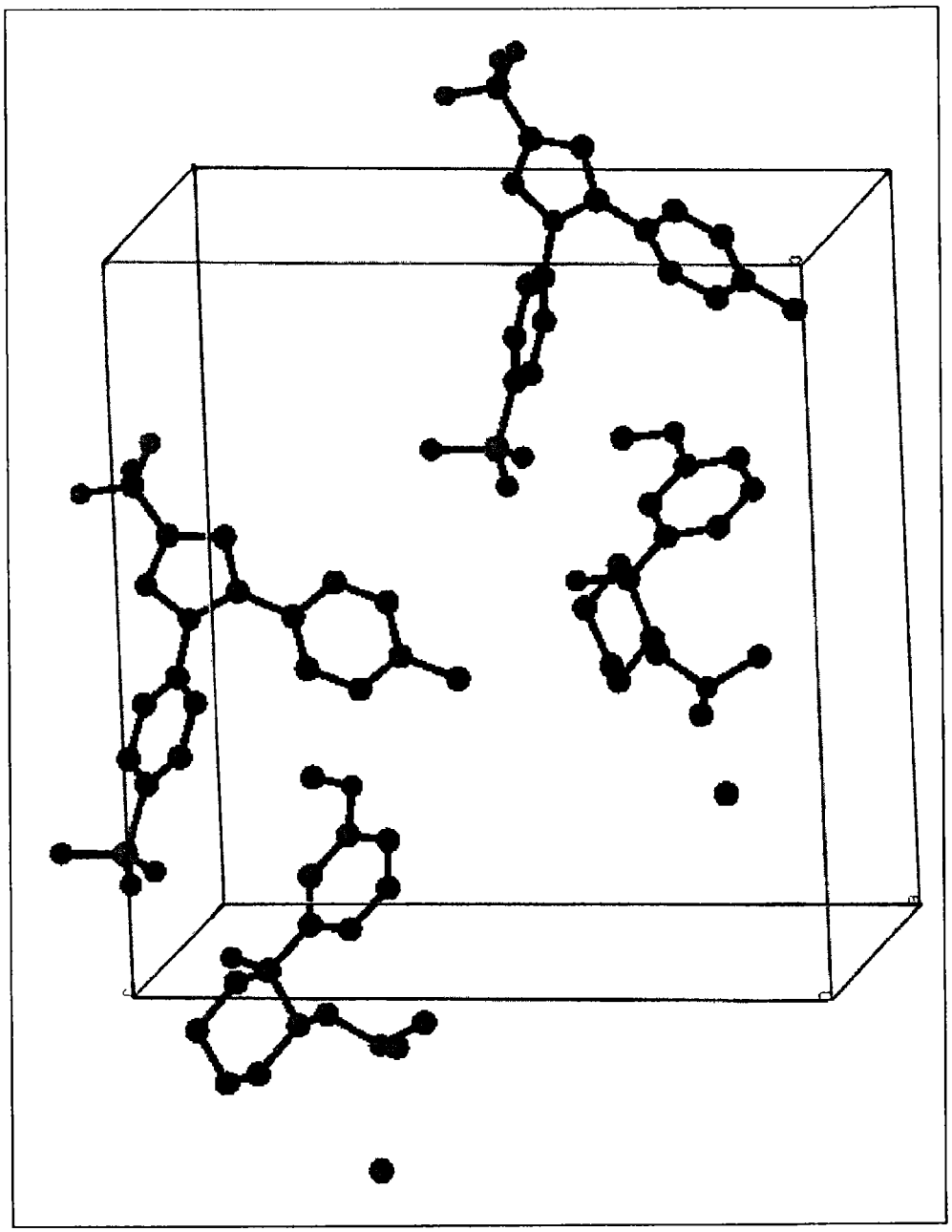
FIG. 11:
Structure of the unit cell of the (rac)-tramadol.HCl-celecoxib 1:1 co-crystal obtained by SCXRD analysis showing two molecules of celecoxib and two molecules of tramadol.

The TG analysis of the crystalline form according to the invention shows insignificant weight loss between 30 and 200° C.
Single Crystal XRD Analysis of a Single Crystal of a Co-Crystal of (Rac)-Tramadol.HCl and Celecoxib (1:1) (See FIG. 11):

The crystal structure was determined from single crystal X-ray diffraction data. The colourless prism used (0.33×0.16×0.11 mm) was obtained from the crystallization of a seeded solution in heptane and IPA of equimolar amounts of (rac)-tramadol hydrochloride and celecoxib.

Analysis was performed at room temperature using a Bruker Smart Apex diffractometer with graphite monochromated Mo K$_\alpha$ radiation equipped with a CCD detector. Data were collected using phi and omega scans (program used: SMART 5.6). No significant decay of standard intensities was observed. Data reduction (Lorentz and polarization corrections) and absorption correction were applied (program used: SAINT 5.0).

The structure was solved with direct methods and least-squares refinement of F$_o^2$ against all measured intensities was carried out (program used: SHELXTL-NT 6.1). All non-hydrogen atoms were refined with anisotropic displacement parameters. Crystal data and structure refinement for (rac)-tramadol-celecoxib (1:1) co-crystal is given in the following table 5.

TABLE 5

Most relevant structural data of the SCXRD analysis of a co-crystal of (rac)-tramadol•HCl-celecoxib (1:1).

| | |
|---|---|
| Crystal system | Orthorhombic |
| Space group | Pna2$_1$ |
| a (Å) | 11.0323(7) |
| b (Å) | 18.1095(12) |
| c (Å) | 17.3206(12) |
| Volume (Å³) | 3460.5(4) |
| Z | 4 |
| D calc. (Mg/m³) | 1.308 |
| N. of refl. | 8336 |
| Refl. with I > 2σ(I) | 5240 |
| R (I > 2σ(I)) | 0.0584 |

The crystal structure is depicted in FIG. 12 (only half of the unit cell contents is shown, hydrogen atoms have been omitted for clarity; program used: Mercury 2.2, C. F. Macrae, I. J. Bruno, J. A. Chisholm, P. R. Edgington, P. McCabe, E. Pidcock, L. Rodriguez-Monge, R. Taylor, J. van de Streek and P. A. Wood, J. Appl. Cryst., 41, 2008, 466-470).

Simulation of XRPD diffractogram from single crystal data gives an almost identical diagram to the experimental one presented above.

Example 4c

Determination of the Bioavailability of Co-Crystal of (Rac)-Tramadol.HCl-Celecoxib (1:1)

The objective is to measure plasma exposure in rat of (rac)-tramadol.HCl and celecoxib by means of AUC determination of the co-crystal of (rac)-tramadol.HCl-celecoxib (1:1) of the present invention, and comparing it with each active principle of the co-crystal and the fixed combination of the two active principles.

Bioavailability of (rac)-tramadol.HCl-celecoxib co-crystal is compared to those obtained after administration of tramadol.HCl plus celecoxib, combined and separately, to rats by oral route. Products with an equivalent particle size are orally administered by means of rodent capsules at a dose level of 25 mg/kg of co-crystal and at an equivalent dose level of comparators (11 mg tramadol.HCl/kg, 14 mg celecoxib/kg). Blood from rats is extracted at the following time points: predose, 15, 30, 45 min, 1, 1.5, 2, 3, 4, 5, 6, 8 and 24 h. Plasma is isolated by centrifugation, purified by SPE and plasma levels are determined by LC-MS-MS. Pharmacokinetic parameters are calculated using non-compartmental pharmacokinetic analysis.

The results show an increase exposure of celecoxib when the co-crystal (rac)-tramadol.HCl-celecoxib is administered compared to celecoxib alone and to the combination of both API's (the mixture of tramadol and celecoxib).

The invention claimed is:
1. A co-crystal comprising tramadol either as a free base or as a physiologically acceptable salt and at least one NSAID, wherein the NSAID is naproxen, its enantiomers or salts thereof, wherein the molecular ratio between the tramadol and naproxen is 1:2, and comprising (−)-tramadol either as a free base or as a physiologically acceptable salt and (S)-naproxen or comprising (+)-tramadol either as a free base or as a physiologically acceptable salt and (R)-naproxen, or mixture of enantiomers of these co-crystals, characterized in that it has a monoclinic unit cell with the following dimensions:
a=9.512(2) Å
b=40.5736(11) Å c=10.323(4) Å
α=90°
β=96.29(1)°
γ=90°.

2. Pharmaceutical composition wherein said composition comprises a therapeutically effective amount of the co-crystal according to claim 1 in a physiologically acceptable medium.

3. A method for the treatment of pain comprising administering to a subject in need thereof a therapeutically effective amount of at least one co-crystal according to claim 1 comprising tramadol either as a free base or as a physiologically acceptable salt and naproxen, its enantiomers or salts thereof.

4. A method according to claim 3, wherein said pain is selected from acute pain, chronic pain, neuropathic pain, severe to moderate pain, hyperalgesia, allodynia, cancer pain, diabetic neuropathy, diabetic peripheral neuropathy, osteoarthritis, fibromyalgia, rheumatoid arthritis, ankylosing spondylitis, frozen shoulder and sciatica.

5. Process for the production of a co-crystal according to claim 1 comprising the steps of:
   (a) dissolving or suspending naproxen in a solvent optionally heating the solution or dispersion to a temperature above ambient temperature and below the boiling point of the solution or dispersion;
   (b) dissolving together with, or after, or before step (a) tramadol either as a free base or as a salt in a solvent, optionally combined with step (a) by dissolving tramadol already together with the naproxen in step (a)
   (c) optionally adding the solution of (b) to the solution of (a) and mixing them;
   (d) optionally adding a solvent to the solution/dispersion of (a), (b) or (c) and mixing them;
   (e) cooling the mixed solution/dispersion of step (a), (b), (c) or (d) to ambient temperature or below;
   (f) optionally evaporating part or all of the solvent; and
   (g) filtering-off the resulting co-crystals.

6. A co-crystal comprising tramadol either as a free base or as a physiologically acceptable salt and at least one NSAID, wherein the NSAID is naproxen, its enantiomers or salts thereof, wherein the molecular ratio between the tramadol and naproxen is 1:2, and comprising (−)-tramadol either as a free base or as a physiologically acceptable salt and (S)-naproxen or comprising (+) tramadol either as a free base or as a physiologically acceptable salt and (R)-naproxen, or enantiomeric mixtures of these co-crystals, characterized in that it shows a Powder X-Ray Diffraction pattern with peaks [2θ] at 8.7, 9.5, 12.7, 18.7, and 20.1 [°], with the 2θ values being obtained using copper radiation ($Cu_{K\alpha 1}$ 1.54060 Å).

7. A co-crystal according to claim 6, characterized in that it shows a Powder X-Ray Diffraction pattern with peaks [2θ] at 8.7, 9.5, 10.6, 11.3, 12.1, 12.7, 13.7, 18.7, and 20.1 [°], with the 2θ values being obtained using copper radiation ($Cu_{K\alpha 1}$ 1.54060 Å).

8. A co-crystal according to claim 7, characterized in that it shows a Powder X-Ray Diffraction pattern with peaks [2θ] at 4.3, 8.7, 9.5, 10.2, 10.6, 11.3, 12.1, 12.7, 13.2, 13.7, 14.3, 14.6, 14.8, 15.5, 15.7, 16.0, 16.2, 17.0, 17.4, 17.9, 18.1, 18.7, 19.1, 19.4, 19.7, 20.1, 20.5, 20.8, 21.1, 21.4, 21.6 and 21.8 [°], with the 2θ values being obtained using copper radiation ($Cu_{K\alpha 1}$ 1.54060 Å).

9. Pharmaceutical composition wherein said composition comprises a therapeutically effective amount of the co-crystal according to claim 6 in a physiologically acceptable medium.

10. Pharmaceutical composition wherein said composition comprises a therapeutically effective amount of the co-crystal according to claim 7 in a physiologically acceptable medium.

11. Pharmaceutical composition wherein said composition comprises a therapeutically effective amount of the co-crystal according to claim 8 in a physiologically acceptable medium.

12. A method for the treatment of pain comprising administering to a subject in need thereof a therapeutically effective amount of at least one co-crystal according to claim 6 comprising tramadol either as a free base or as a physiologically acceptable salt and naproxen, its enantiomers or salts thereof.

13. A method according to claim 12, wherein said pain is selected from acute pain, chronic pain, neuropathic pain, severe to moderate pain, hyperalgesia, allodynia, cancer pain, diabetic neuropathy, diabetic peripheral neuropathy, osteoarthritis, fibromyalgia, rheumatoid arthritis, ankylosing spondylitis, frozen shoulder and sciatica.

14. Process for the production of a co-crystal according to claim 6 comprising the steps of:
   (a) dissolving or suspending naproxen in a solvent optionally heating the solution or dispersion to a temperature above ambient temperature and below the boiling point of the solution or dispersion;
   (b) dissolving together with, or after, or before step (a) tramadol either as a free base or as a salt in a solvent, optionally combined with step (a) by dissolving tramadol already together with the naproxen in step (a)
   (c) optionally adding the solution of (b) to the solution of (a) and mixing them;
   (d) optionally adding a solvent to the solution/dispersion of (a), (b) or (c) and mixing them;
   (e) cooling the mixed solution/dispersion of step (a), (b), (c) or (d) to ambient temperature or below;
   (f) optionally evaporating part or all of the solvent; and
   (g) filtering-off the resulting co-crystals.

* * * * *